(12) United States Patent
Williams et al.

(10) Patent No.: US 7,588,763 B2
(45) Date of Patent: Sep. 15, 2009

(54) METHODS FOR THE PREVENTION AGAINST OR TREATMENT OF DIABETES WITH ETXB AND/OR INSULIN

(75) Inventors: Neil Andrew Williams, Axbridge (GB); Timothy Raymond Hirst, Clevedon (GB); Toufic Osman Nashar, Bristol (GB)

(73) Assignee: Trident Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 11/240,134

(22) Filed: Sep. 30, 2005

(65) Prior Publication Data

US 2006/0083751 A1  Apr. 20, 2006

Related U.S. Application Data

(62) Division of application No. 09/867,914, filed on May 30, 2001, now abandoned.

(51) Int. Cl.
*A61K 38/00* (2006.01)
*A61K 39/00* (2006.01)
*C07K 14/195* (2006.01)
*C07K 14/245* (2006.01)

(52) U.S. Cl. .......... 424/184.1; 514/2; 514/885; 530/300; 530/868; 424/185.1

(58) Field of Classification Search .......... None
See application file for complete search history.

(56) References Cited

U.S. PATENT DOCUMENTS

| | | | | |
|---|---|---|---|---|
| 5,554,378 | A | 9/1996 | Uda et al. | 424/434 |
| 5,714,459 | A | 2/1998 | O'Brien et al. | 514/2 |
| 6,287,563 | B1 * | 9/2001 | Williams et al. | 424/184.1 |
| 2001/0036917 | A1 | 11/2001 | Williams | |

FOREIGN PATENT DOCUMENTS

| | | |
|---|---|---|
| AU | 724516 | 9/2000 |
| CA | 2084120 | 5/1994 |
| CA | 2225788 | 1/1997 |
| CN | 1192693 | 9/1998 |
| DE | 69633393 | 11/2005 |
| DK | 0841939 | 1/2005 |
| EP | 0841939 | 5/1998 |
| ES | 2229276 | 4/2005 |
| HK | 1006496 | 4/2005 |
| MX | 9800241 | 11/1998 |
| NZ | 311762 | 4/2001 |
| PL | 324424 | 5/1998 |
| RU | 2203088 | 4/2003 |
| SI | 0841939 | 4/2005 |
| WO | WO 95/10301 | 4/1995 |
| WO | 9702045 | 1/1997 |
| WO | WO 9958145 | 11/1999 |
| WO | WO 0014114 | 3/2000 |

OTHER PUBLICATIONS

Wooley et al. Database Medline, DN 95283386; Annals of the Rheumatic Diseases, Apr. 1995,54 (4), 298 304.
Amin et al. Protein Expression and Purification 5, 198-204, 1994.
Ochi et al. Database Caplus, DN 121:170550. CA Patent 2,084,120, May 1994.
Azipurua, H.J., and Russell-Jones, G.R., J. Exp. Med. 167: 440-451 (1988).
Brocke, S., et al., Nature 365: 642-644 (1993), abstract only.
Craig, S.W., and Cuatrecasas, P., Proc. Nat Acad. Sci. USA 72: 3844-3848 (1975).
Elson, C.O., et al., J. Immunol. Meth. 67: 101-108 (1984).
Elson, C.O., et al., J. Immunol. 154: 1032-1040 (1995).
Francis, M.L., et al., J. Immunol. 148: 1999-2005 (1992).
Imboden, J.B., et al., Proc. Nat. Acad. Sci. USA 83: 5673-5677 (1986).
Jenkins, M.K., and Johnson, J.G., Curr. Op. Immunol. 5: 361-367 (1993).
Kaper, J.B., et al., Nature 308: 655-658 (1984), abstract only.
Meyer, O., Presse Medicale 24: 1171-1177 (1995), abstract only.
Micusan, V. V., and Thibodeau, J., Seminars in Immunology 5: 3-11 (1993),abstract only.
Nashar, T.O., et al., Proc. Nat. Acad. Sci. USA 93: 226-230, 1996.
Nashar, T.O., et al., Internat. Immunol. 8: 731-736 (1995).
O'Connor, P.M., Cancer Res. 53: 4776-4780 (1993).
Sandkvist, M., et al., J. Bact. 169: 4570-4576 (1987).
Sun, D., J. Neuroimmunol. 46: 5-10 (1993), abstract only.
Yankelevich, B., et al., J. Immunol. 154: 3611-3617 (1995).
Yu, J., et al., Molec. Microbiol. 6: 1949-1958 (1992).

(Continued)

Primary Examiner—Michael Borin
(74) Attorney, Agent, or Firm—Mintz, Levin, Cohn, Ferris, Glovsky and Popeo, P.C.

(57) ABSTRACT

This application relates to methods for modulating an immune response in a mammalian subject in need of prevention against or treatment of diabetes comprising the administration of EtxB and/or insulin.

26 Claims, 28 Drawing Sheets

OTHER PUBLICATIONS

Beech, J.T., Bainbridge, T., and Thompson, S.J. (1997), Journal of Immunological Methods, 205: 163-168.

Nashar, T.O., and Hirst, T. R. (1995), Vaccine, 13(9): 803-810.

Ploix, C., Bergerot, I., Durand, A., Czerkinsky, C., Holmgren, J., and Thivolet, C. (1999), Diabetes, 48: 2150-2156.

Wang, B., Andre, I., Gonzalez, A., Katz, J. D., Aguet, M., Benoist, C., and Mathis, D. (1997), Proc. Natl. Acad. Sci., 94: 13844-13849.

Wicker, L. S., Miller, B. J., and Mullen, Y. (1986), Diabetes, 35: 855-860.

Wong, F. S., and Janaway, C. A. (1999), Curr. Opinion in Immunology, 11:643-647.

* cited by examiner

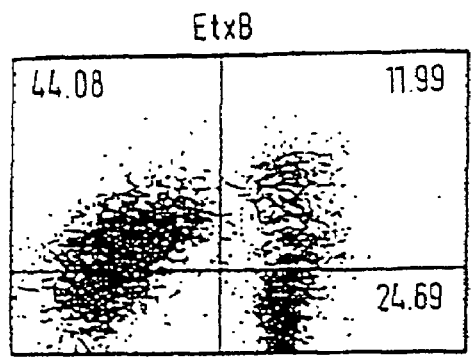
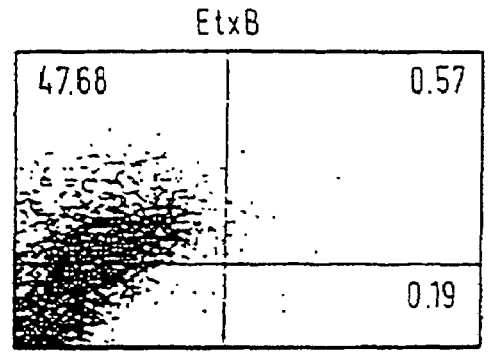
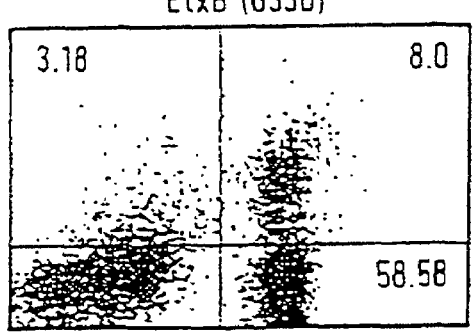
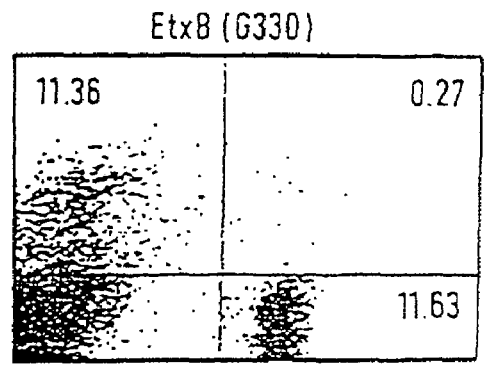
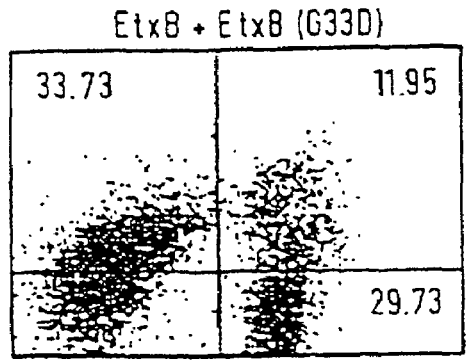
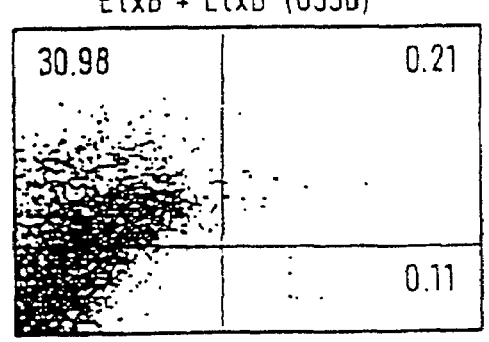
FIG. 5

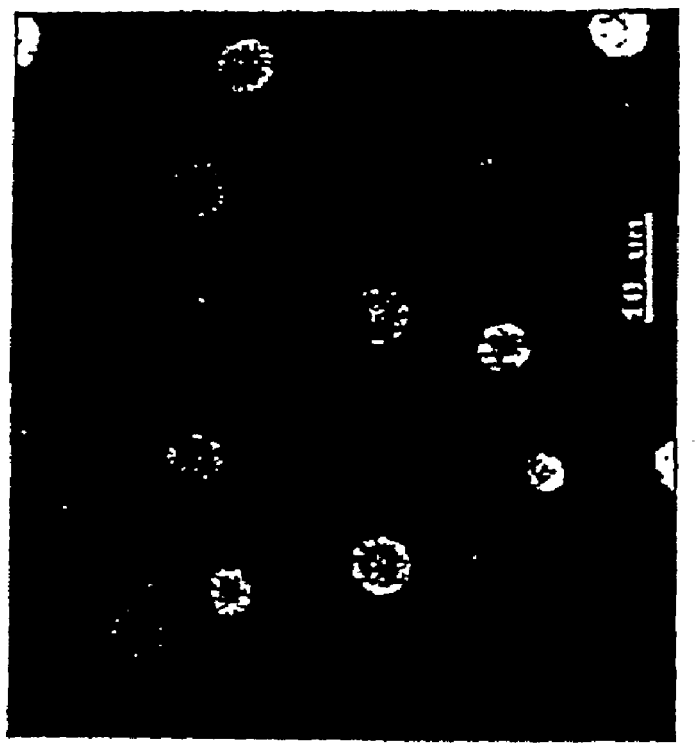
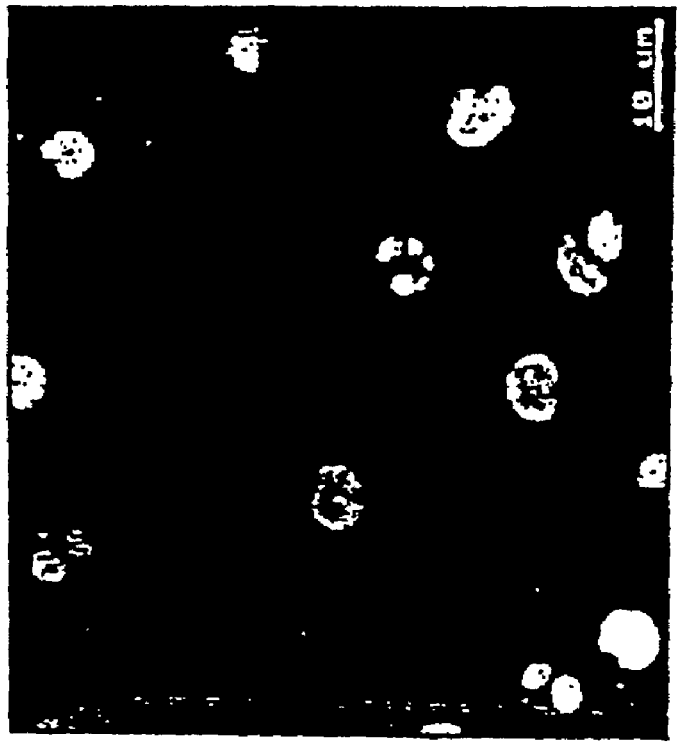
FIG. 7

FIG. 10
GM1-MEDIATED APOPTOSIS OF HUMAN PERIPHERAL BLOOD MONONUCLEAR CELLS

FIG. 11
GM1-MEDIATED APOPTOSIS OF AN IMMORTALISED MURINE T-CELL LINE, CTLL

Fig. 18

Fig. 19

|  | Untreated | Diabetic (unprotected) mice | Protected mice |
|---|---|---|---|
| γIFN (ng/ml) | 1.022+/-0.3 | 1.683+/-0.06 | 0.091+/-0.005 |
| IL-4 (pg/ml) | 30 +/- 2 | 31+/-2 | 38+/-2 |
| IL10 (pg/ml) | 30+/-3 | 38+/-23 | 135+/-6 |

Fig. 21

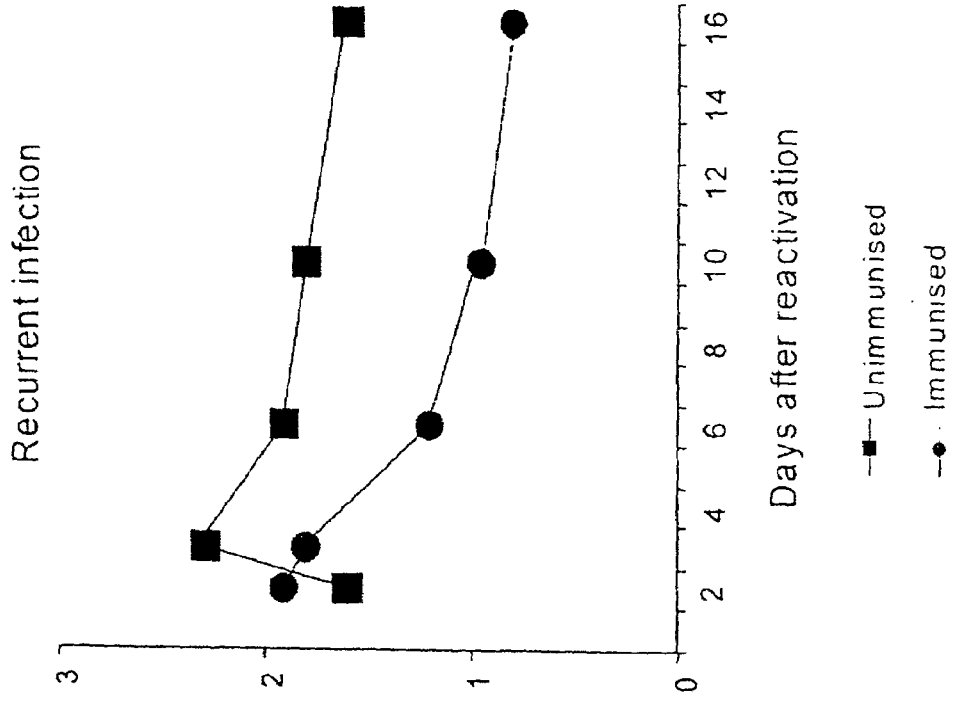
Fig. 22a Primary infection
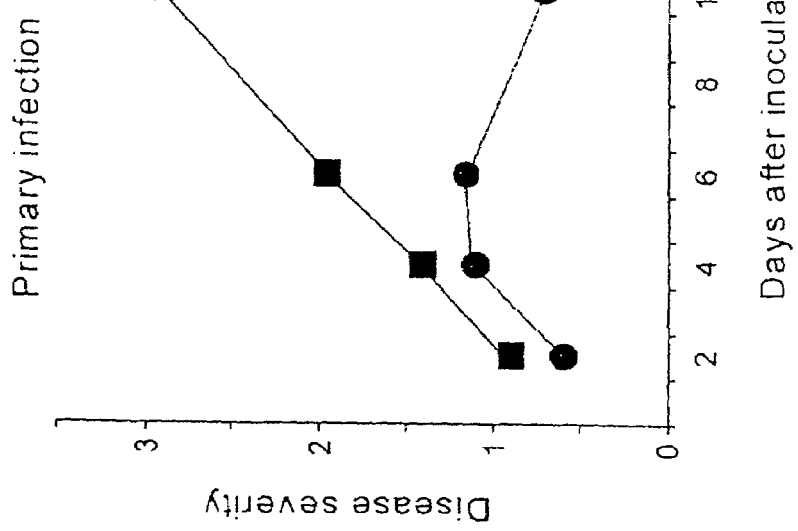
Fig. 22b Recurrent infection

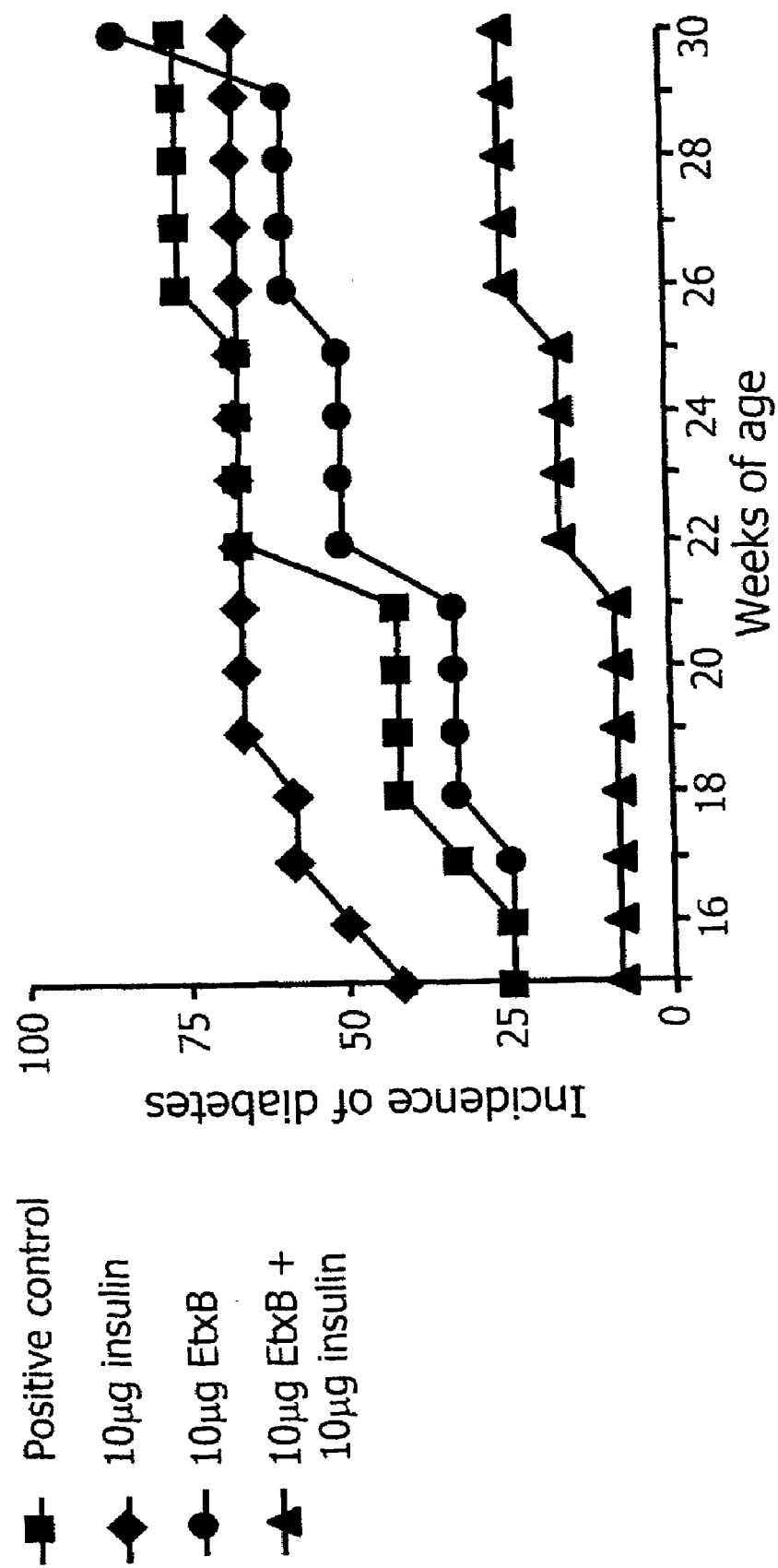

METHODS FOR THE PREVENTION AGAINST OR TREATMENT OF DIABETES WITH ETXB AND/OR INSULIN

CROSS-REFERENCES TO RELATED APPLICATIONS

This application is a Division of U.S. application Ser. No. 09/867,914, filed May 30, 2001, now abandoned, which is incorporated herein by reference in its entirety.

BACKGROUND OF THE INVENTION

1. Field of the Invention

This invention relates to therapeutic agents for use in the treatment of mammalian, particularly human, autoimmune diseases. The invention also relates to therapeutic agents useful in the treatment of human leukaemias of a T cell origin, as so-called "vaccine carriers", and as agents for use in the prevention of human transplantation rejection and graft versus host disease (GVHD).

2. Description of the Related Art

In an article entitled "Morphologic and Functional Alterations of Mucosal T Cells by Cholera Toxin and its B subunit" by Charles O. Elson et al., The Journal of Immunuology, 1995, 154; 1032-1040 it is disclosed that the cholera toxin (Ctx) and the CtxB subunit inhibit $CD8^+$ and $CD4^+$ T cells.

Reference is also made to the paper entitled "Prevention of Acute Graft-Versus-Host Disease by Treatment with a Novel Immunosuppressant" by B. Yankelevich et al., The Journal of Immunology, 1995, 154: 3611-3617. This identifies CtxB as an agent for use in bone marrow transplantation for the prevention of acute graft-versus-host disease (GVHD). WO 95/10301 discloses an immunological tolerance-inducing agent comprising a mucosa-binding molecule linked to a specific tolerogen.

As used herein, the term "Ctx" refers to the cholera toxin and "CtxB" to the B subunit of the cholera toxin. In other texts, these may sometimes be identified as "CT" or "Ct" and "CTB" or "CtB" respectively. The term "Etx" herein means the E. coli heat labile enterotoxin, and "EtxB" is the B subunit of Etx. In other texts, these may sometimes be identified as "LT" or "Lt" and "LtB" or "LtB" respectively.

E. coli enterotoxin. As mentioned above, the term. Etx refers to the heat labile E. coli enterotoxin which is a member of a family of toxins that includes cholera toxin and which cause diarrhoeal diseases in humans and domestic animals. Such toxins are comprised of two components, the so called A and B-subunits. The ability to cause diarrhoea resides with properties of the A-subunit, which is an enzyme capable of increasing the concentration of the biochemical second messenger cyclic AMP within epithelial cells lining the intestine. The rise in cyclic AMP levels leads to the loss of ions from the cells and the consequent loss of water which causes diarrhoea. The B-subunit moiety has evolved in order to deliver the A-subunit into epithelial cells by a process which involves it binding to a membrane located glycolipid receptor, GM1. The B-subunit is itself not toxic, and is unable to cause diarrhoea.

EtxB. The B-subunit is composed of five individual polypeptides bound tightly together into a doughnut ring like structure. Each polypeptide contains a site for interaction with GM1, and thus exposure of cells to EtxB causes cross-linking of GM1 at the cell surface. The overall size of EtxB is 60 kilodaltons, with each of the five polypeptides being composed of 103 amino acids. Its exceptional stability results from the very close association of interfaces between adjacent polypeptides which form the B-subunit pentamer. Thus EtxB is stable as a pentamer under conditions which would lead to disruption of normal protein structure. This stability is reflected by the observation that the pentamer remains intact at 84° C., between pH 2 and pH 11, and in the presence of ionic detergents and proteolytic enzymes. This makes EtxB one of the most stable protein complexes known and may facilitate ease of use as a component in human medicines.

The key finding that EtxB can alter immune responses has come from investigations of its binding to GM1 on cells other than those of the intestinal epithelium. GM1 is found on all cells of the immune system, and its cross-inking by EtxB triggers signals which can alter their activity. Administration of EtxB either into the nose, by mouth, or by injection, can alter the local environment within which immune responses are triggered. This facilitates the production of high levels of antibodies against antigens of infectious agents which are mixed with EtxB, and can cause the down-regulation of the damaging inflammatory responses which are associated with autoimmunity. Thus, EtxB may be used: alone in the treatment of autoimmune disease (as an immunotherapeutic), or in combination with vaccine antigens (where it acts as an adjuvant). The ability to act as an adjuvant following mucosal delivery makes the B-subunit almost unique since most infectious agents gain access to the body through these surfaces, and injected vaccines do not stimulate strong responses at such sites.

The immunological mechanisms underlying the use of the B-subunit. The B-subunits ability to modulate the immune response is dependent on its capacity to modulate the activity of T-cells, B-cells and populations of antigen presenting cells. Each of these cell types plays a critical role in the development of the immune response. In the normal response to a foreign organism, antigens are internalised by antigen presenting cells, of which dendritic cells are the most important. These cells are specialised in breaking down proteins into short amino acid sequences (peptides) which associate with major histocompatibility complex (MHC) molecules which are then transported to the cell surface.

Foreign peptides bound to class II MHC molecules are recognised by T-helper cells (CD4+ T-cells) which are activated as a result and begin to divide, differentiate and secrete hormone-like messengers called cytokines. The T-helper cells then co-ordinate and maintain the immune response. Subsequent responses can involve the activation of i) B-cells which mature into plasma cells capable of producing antibodies, ii) macrophages and neutrophils which enter the sites of infection and ingest foreign material leading to its destruction, and iii) other types of T-cell (CD8+ T-cells) which can recognise virally infected cells of the body and kill them.

Most normal immune responses will involve activation of all of these components to some extent, however, it is clear that certain factors can affect which particular components are dominant. Further, in certain circumstances it is clearly beneficial to be able to tailor which type of response is elicited. For example, in preventing infection at mucosal surfaces, it is desirable to stimulate a strong antibody response, but avoid the activation of macrophages and neutrophils which can themselves cause inflammation and tissue damage.

In order to co-ordinate different types of immune response, humans have evolved the capacity to sense the nature of the foreign challenge and alter the T-helper cell response accordingly. Thus, T-helper cells can be distinguished as being either T-helper 1 (Th1) or T-helper 2 (Th2) cells. Th1 cells secrete cytokines including gamma interferon (IFNγ) and interleukin (IL)-2 which activate macrophages, neutrophils and CD8+ T-cells and which lead to the production of antibodies which promote inflammation. In contrast, Th2 cells secrete IL-4, IL-5, IL-6 and IL-10, down-regulate Th1 responses and promote the production of antibodies which are secreted at mucosal surfaces, or which do not trigger inflammation. In addition to the cross-regulation of Th1 responses by Th2 cells and vice versa, it is also clear that other CD4+ T-cell populations are induced which down-regulate both types of response (T-regulatory cells). In, for example, an immune response to a virus which infects the eye, it is desirable to trigger a strong Th2 response which can arm the local tissue with antibodies to block the infection, while avoiding stimulating Th1 responses which will themselves cause damage to such a delicate tissue.

Autoimmune disease results when the bodies own processes of regulation breakdown. In these cases components of the body are mistakingly identified as 'foreign' and an immune response is mounted which attacks the individuals own tissues. In the majority of examples of autoimmune disease, tie immune response is driven by Th1 cells which cause macrophages and neutrophils to enter and disrupt the tissue. For example, in the case of rheumatoid arthritis an immune response to joint-associated antigens leads to the chronic infiltration of neutrophils and macrophages which cause cartilage and bone degradation, pain, swelling and loss of function. Further, type 1 diabetes results from a similar process leading to the destruction of insulin producing islets within the pancreas. The precise reasons for the loss of regulation within the immune systems of certain individuals are not clear, but certainly involve complex genetic and environmental factors.

The B-subunit influences the processes involved in antigen recognition by T-helper cells. In doing so it can promote the activation of Th2 and T-regulatory cells, while at the same time suppressing the activation of Th1 cells. Consequently, EtxB may be used to treat Th1-driven autoimmune diseases, or may be added to antigens derived from infectious agents to trigger production of large quantities of protective mucosal and serum Th2-associated antibodies. Importantly, EtxB does not promote the production of IgE antibodies which are the cause of allergy.

The B-subunit alters the balance between Th1 and Th2 immune responses. It is clear that the local microenvironment in which antigen is presented to CD4+ T-cells determines the nature of the subsequent response (FIG. 12). Certain factors can promote the differentiation of T-helper cells into Th1 cells, while others cause differentiation into Th2 cells or T-regulatory cells. Evidence indicates that EtxB influences many of these events. The differentiation of T-helper cells into Th1 cells is promoted by cytokines produced by antigen presenting cells themselves (in particular, dendritic cell and macrophage derived IL-12) as well as CD8+ T-cells (producing gamma interferon).

The present inventors have established that EtxB inhibits the production of IL-12 by antigen presenting cells (FIG. 13) and removes CD8+ T-cells by causing them to die by apoptosis (FIG. 14). Therefore, EtxB interferes with the two major factors which promote the development of pro-inflammatory Th1 responses. The differentiation of T-helper cells into Th2 cells is promoted by their interaction with B-cells during the activation process, and by the secretion of IL-10 from antigen presenting cells. IL-10 is also thought to play a critical role in the generation and activities of T-regulatory cells. The present inventors have shown that EtxB activates B-cells leading to their enhanced interaction with T-helper cells (FIG. 15), and causes the production of IL-10 by antigen presenting cells (FIG. 16). Thus, EtxB enhances the presence of the two major factors which promote the activation of Th2 cells and creates conditions which favour the induction of regulatory cell populations.

Taken together, the activities of EtxB allow it to shift the balance of the immune response suppressing the Th1 arm while promoting the Th2 and T-regulatory anus (FIG. 12). Thus, EtxB can turn off the damaging inflammation in autoimmunity, and can trigger the production of non-inflammatory antibodies in the serum and at mucosal surfaces.

The B-subunit can be used to prevent or treat autoimmune disease. The ability of EtxB to intervene in the processes underlying autoimmune disease has been tested in animal models of arthritis. Usefulness in the treatment or prevention of arthritis has been established using a widely recognised mouse model in which disease is induced in male DBA/1 mice by the injection of type II collagen in complete Freunds adjuvant (collagen-induced arthritis). Mixing a joint antigen in this way with an adjuvant which triggers strong Th1 responses leads to a strong pro-inflammatory immune response against collagen. This response is characterised by the appearance of anti-collagen antibodies and demonstrable T-cell reactions. By day 20 after induction, joint swelling becomes apparent and its incidence and severity continues to increase until approximately day 45 at which point 70-80% of animals have some swelling, usually involving the hind ankle and knee joints. Damage is also occasionally noted in the forelimbs. Like rheumatoid arthritis in humans, the model is characterised by joint swelling and histological signs of macrophage and neutrophil infiltration into the joint space. In addition, cartilage and bone destruction are a common feature along with the formation of a pannus. Assessment of the immune response to collagen in mice with arthritis reveals the presence of pro-inflammatory antibodies as well as high levels of the Th1 cytokine, gamma interferon, in cultures of lymph node T-cells.

Collagen induced arthritis (CIA) can be prevented by treatment with EtxB alone. When EtxB is given to mice intranasally, orally or by injection prior to the collagen injection, it can block the induction of disease as revealed by a reduction in clinical joint swelling (FIG. 17) and histological damage (FIG. 18). In the experiments shown, EtxB was administered into the nose or by mouth on four occasions daily up to the day of collagen injection. Injected EtxB was given on a single occasion on the day of collagen challenge.

In each case the dose of EtxB used was 100 μg. Investigations have shown that in the case of nasal delivery identical levels of disease protection can be achieved with 10 μg, or 1 μg. The delivery of EtxB led to a dramatic reduction in pro-inflammatory anti-collagen antibody levels and led to a shift in the nature of the T-helper cell response away from the production of gamma interferon.

The B-Subunit can be used as a potent mucosal vaccine adjuvant. The need to potentiate immune responses to vaccine antigens is widely recognised. At present the only adjuvant licensed for human use is alum, which is given by injection and fails to elicit significant mucosal antibody production. Given that the majority of infectious disease causing organisms enter across mucosal surfaces, it is clear that an effective mucosal adjuvant will have widespread applications. The present inventors have shown that EtxB is a highly potent adjuvant which can stimulate strong immunity to foreign antigens after mucosal administration. Important work has been carried out by the present inventors (see WO 99/58145) using a mouse model of herpes simplex virus type 1 (HSV-1) infection of the eye.

Herpes simplex virus type 1 infection usually occurs in early childhood and affects over 90% of adults. The initial infection is usually unnoticed, although occasionally can cause severe disease. However, following initial infection the virus resides, dormant, in the nervous system which supplies the face and eyes. In some people HSV can reactivate and leads to disease in any of these areas. On the skin HSV-1 causes 'cold sores' which are usually self-limiting, although unpleasant. However, when virus enters the eye, it causes ulcers on the surface of the eye which can result in blindness and the need for corneal transplantation. HSV-1 is the major cause of post-infection blindness in the developed world. A close relative of HSV-1, HSV-2, is associated with similar, although more severe, infections of the genital tract.

When a glycoprotein mixture from HSV-1 is given to alone to mice intranasally, it fails to induce an immune response to HSV. By contrast, the addition of EtxB to this glycoprotein mixture potentiates a very strong response involving the secretion of large amounts of anti-HSV antibody into the serum and at mucosal surfaces (FIG. 21). The antibody response is clearly evident both at the eye as well as at distant sites including the vagina. The underlying T-helper cell response to HSV is associated with the production of predominantly Th2 cytokines. The immune response induced using EtxB as a mucosal adjuvant can protect mice against a severe ocular HSV-1 infection (FIG. 22a). In the model, the vaccine, when given prior to challenge with HSV-1 reduces the severity of symptoms in the eye and prevents the high levels of viral spread to the central nervous system (a rare complication in humans). These findings demonstrate that EtxB can be used as an adjuvant for a prophylactic vaccine against HSV-1.

In further studies, the present inventors have shown that EtxB can be used to develop a therapeutic vaccine against HSV-1. In these experiments mice were infected with HSV-1 and left in order to allow the virus to become dormant in the nervous system prior to vaccination. Intranasal administration of HSV-1 glycoproteins with EtxB altered the nature of the existing response to HSV-1 in these animals such that they showed markedly reduced levels of disease following reactivation of the virus using a physiological stimulus to the eye (FIG. 22b). This additional finding highlights the potential of EtxB as a critical component allowing therapeutic vaccination.

These findings demonstrate that intranasal administration of a vaccine containing EtxB as an adjuvant induces immunity at local and distant mucosal sites. A similar intranasal vaccine using glycoproteins from HSV-2 may be effective in stimulating protective immunity against genital infection. Further, the profile of the immune response stimulated using EtxB is of clear relevance to protection against a wide range of infectious agents. Indeed, experiments have shown that EtxB may be used to stimulate immunity against a broad range of other antigens.

The B-subunit can be used to target the delivery of peptides into cells. The effective induction of cytotoxic T-cell responses requires the entry of antigens into the cytosol of antigen presenting cells. While some externally added soluble antigen may enter this compartment, targeted delivery into the cytosol should augment the induction of this component of the immune response. Cytotoxic T-cell responses are particularly important in facilitating the removal of infectious agents which reside within cells of the body, such as viruses and certain bacteria. Thus, in some vaccines the ability to augment the cytotoxic T-cell response as well as stimulate high levels of antibodies would be beneficial. To achieve this, an efficient delivery system which results in the targeting of antigens into the cytosol is required. The B-subunit exhibits characteristics which indicate that it may function in this way.

Cross-linking of GM1 by the B-subunit is followed by its internalisation into vessicles within the cell. This capacity to enter cells has been used to deliver attached peptides into the cytosol. The present inventors have demonstrated that peptides ranging from nine to twenty seven amino acids in length can be genetically or chemically conjugated to the B-subunit without interfering with its stability or ability to bind to GM1. Addition of such conjugates to cells results in the liberation of the attached peptides within a vessicular compartment and their subsequent delivery to the cytosol. Delivery of EtxB in this way may lead to the presentation of the peptides to stimulate the activation of cytotoxic T-cells.

The B-Subunit is a Lead Compound to the Development of Small Molecule Mimetics.

All of the described effects of EtxB are dependent on its ability to bind to the cell surface. The present inventors have demonstrated in WO 00/14114 that a mutant B-subunit that is unable to bind to the cell surface is completely ineffective. A refinement of this approach has identified a loop with the B-subunit which is responsible for triggering the effects on immune cells. Surprisingly, this loop is not directly involved in allowing binding to GM1, indicating a critical role for interaction with a secondary receptor at the cell surface. A synthetic peptide corresponding to this loop exhibits a similar capacity to modulate T-cell function in vitro. This observation indicates that the loop represents a lead compound for small molecule mimetic chemistry which may allow the development of higher affinity analogues for use as immunotherapeutics and vaccine adjuvants.

Diabetes. Insulin dependent diabetes mellitus (IDDM) is an autoimmune disease resulting form the T-cell dependent destruction of insulin-producing cells from the pancreas Langerhans islets (1). It affects about 4 million people in Europe and North America alone and usually appears before the age of 30. There is no cure. Sufferers must give themselves daily insulin injections to control their blood glucose levels. It is unclear what triggers the immune system's attack on the islet cells because the regulation of the auto-aggressive immune response is complex, resulting from the interaction between several T cell subsets and their activation of mononuclear phagocytes. Islet destruction, both in humans and rodents, is attributed to the existence of auto-reactive CD4+T cells that recognise islet antigens and belong to the Th1 subset (i.e. secrete inflammatory cytokines such as IFN$\gamma$) (2). Such cells could be isolated from diabetic rodent spleens or pancreas inflammatory infiltrates and transferred the disease to syngenic receipents (3).

The present invention seeks to provide an improved mechanism for preventing and treating IDDM.

SUMMARY OF THE INVENTION

The effectiveness of the B-subunit in treating autoimmune diabetes has been established using the NOD mouse model in which disease arises spontaneously at between 14 and 25 weeks of age. As in human type I diabetes, disease in the NOD is influenced by complex genetic and environmental factors which allow the development if an immune response to several pancreatic antigens. The mice develop a non-specific insulitis (immune infiltration of the pancreas) at between 6 and 8 weeks of age, and this leads to progressive islet destruction such that 70 to 80% become diabetic. Diabetes is readily demonstrated by the presence of high glucose levels in the urine or blood.

The present invention demonstrates the surprising finding that: (i) when a sub-optimal insulin administration protocol was used (6×10 ug doses on alternate days over 2 weeks in NOD mice at 6 weeks of ace) NOD mice were not protected from the development of IDDM; (ii) when similar doses of EtxB, were administered i.n. according to the same schedule, this did not prevent the development of IDDM in the NOD mice. However, when EtxB was admixed insulin according to the same schedule, this lead to a decreased incidence of IDDM. The prevention of IDDM following administration of EtxB admixed with insulin at 6 weeks, was associated with a clear Th1 to Th2 switch in the cytokine profile of pancreatic T cells responding to TCR engagement.

In addition, the present invention also demonstrates the surprising finding that the late administration of EtxB alone to NOD mice revealed a marked difference in T cell cytokine profiles from those reported above. By way of explanation, the late administration of EtxB to NOD mice at 10-12 weeks of age led to a dramatic reduction in the incidence of IDDM. This dramatic reduction in the incidence of IDDM was also associated with the production of Th1-associated γIFN as was seen with earlier treatment with EtxB+insulin, but this was not associated with a concomitant rise in Th2 cytokine secretion. Instead, the levels of IL-4 were unchanged and IL-10 was not detected either in lymph node cell cultures from treated or untreated animals. These findings suggested that the mechanisms of IDDM prevention by EtxB alone and EtxB+insulin may be different. In this respect, the early administration of EtxB admixed with insulin to NOD mice at 6 weeks of age may result in the EtxB acting as an 'adjuvant' promoting immune deviation away from Th1 associated cytokine responses and towards Th2 associated cytokine responses. In contrast, the late administration of EtxB alone (in the absence of an autoantigen such as insulin) may effectively block diabetes but pancreatic inflammation needs to be established in order for it to do so. In contrast to the T cell cytokine profile associated with early administration of EtxB admixed with insulin, the reduction in the incidence of IDDM by the administration of EtxB alone is associated with the suppression of a Th1 cytokine associated response without promotion of a Th2 cytokine associated response.

In one aspect, the present invention provides a pharmaceutical composition, which comprises an agent of the present invention and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use arc well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the pharmaceutical composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose or chalk, or in capsules or ovules either alone or in admixture with excipients, or in the form of elixirs, solutions or suspensions containing flavouring or colouring agents, or they can be injected parenterally, for, example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Typically, a physician will determine the actual dosage which will be most suitable for an individual subject and it will vary with the age, weight and response of the particular patient and severity of the condition. The dosages below are exemplary of the average case. There can, of course, be individual instances where higher or lower dosage ranges are merited.

The compositions (or component parts thereof) of the present invention may be administered orally. In addition or in the alternative the compositions (or component parts thereof) of the present invention may be administered by direct injection. In addition or in the alternative the compositions (or component parts thereof) of the present invention may be administered topically. In addition or in the alternative the compositions (or component parts thereof) of the present invention may be administered by inhalation. In addition or in the alternative the compositions (or component parts thereof) of the present invention may also be administered by one or more of: parenteral, mucosal, intramuscular, intravenous, subcutaneous, intraocular or transdermal administration means, and are formulated for such administration.

By way of further example, the pharmaceutical composition of the present invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Hence, the pharmaceutical composition of the present invention may be administered by one or more of the following routes: oral administration, injection (such as direct injection), topical, inhalation, parenteral administration, mucosal administration, intramuscular administration, intravenous administration, subcutaneous administration, intraocular administration or transdermal administration.

The invention is illustrated by way of examples in which reference is made to the following Figures.

DESCRIPTION OF THE FIGURES

FIG. 5 illustrates that EtxB causes increased activation of CD4+T cells and depletion of CD8*T cells. The immunization procedure, cell isolation and the in vitro challenge are as described in the legend of FIG. 4. To detect CD25, biotinylated anti-CD25 (7D4) and Streptavidin FITC were used. To detect CD4 and CD8, FITC labelled anti-CD4 (RNRM4-5) and FITC labelled anti-CD8α (53-6.7) were used. Appropriate controls for the antibodies were included (not shown).

FIG. 7 shows that receptor binding by EtxB induces alterations in lymphocyte nuclear morphology characteristic of cells undergoing apoptosis. Mesenteric lymph node cells (MLNC) comprising >90% CD3$^+$ T cells and depleted of macrophages were incubated for 18 h with either 80 μg/ml EtxB or with 80 μg/ml EtxB(G33D) and stained with acridine orange. Cells were examined under conventional or confocal fluorescence microscopy (Leica TCS 4D). A representative microscopic field (×540) for each treatment is shown [EtxB, left hand panel; EtxB (G33D), right hand panel]. Cells which were incubated in the absence of antigen gave similar results to those treated with EtxB(G33D) (not shown).

FIG. 10 shows the results of an experiment conducted to illustrate that EtxB but not EtxB(G33D) induces apoptosis in a population of normal human peripheral blood mononuclear cells.

FIG. 11 shows the results of an experiment which shows that cross-liking of GM1 leads to apoptosis in a proportion of murine CTLL cells.

Figure 1A:
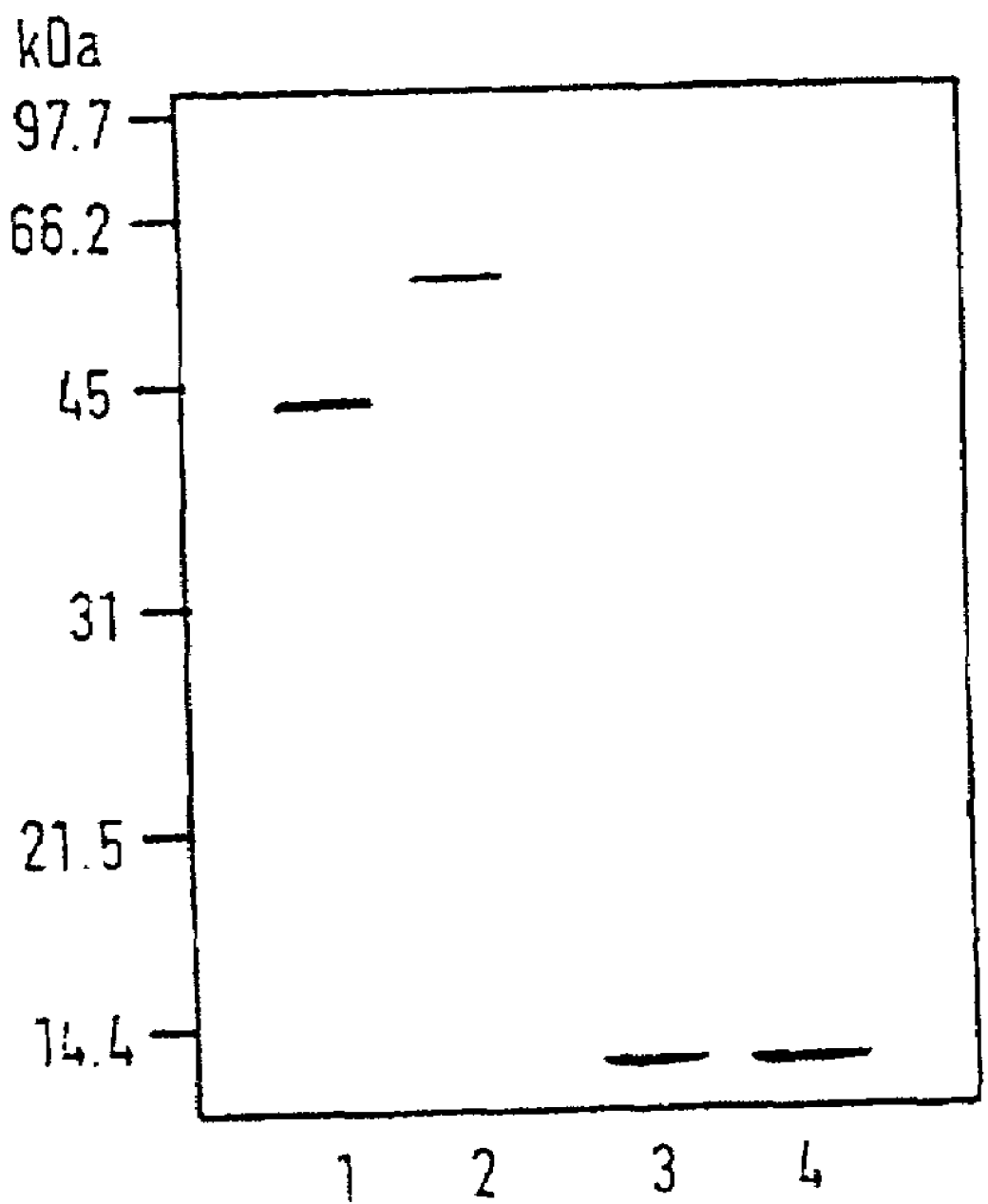
FIG. 1 represents an analysis of physico-chemical properties of EtxB and a mutant form of EtxB, (EtxB(G33D)).
  (A) SDS-PAGE analysis of EtxB or EtxB (G33D): 5 μg of each protein were analysed under reducing conditions in the presence of β-mercaptoethanol with or without prior heating. Lane 1, wild type EtxB, unheated. Lane 2, EtxB (G-33D), unheated. Lane 3; wild type EtxB, heated at 95° C. Lane 4, EtxB (G33D), heated at 95° C. Molecular weight standards (BioRad) are shown on the left-hand side of the panel.
  (B) Determination of apparent molecular mass of EtxB and EtxB (G33D) by gel filtration chromatography: standard curve (circles) was generated using, from top to bottom: bovine serum albumin (66 kDa), hen egg albumin (45 kDa), bovine erythrocyte carbonic anhydrase (29 kDa) and horse heart cytochrome c (12.4 kDa); EtxB and EtxB (G33D) eluted with apparent molecular masses of 36 kDa and 38 kDa respectively; Ve-elution volume of the protein, Vo-void volume of the gel filtration column.
  (C) ELISA for comparative binding of EtxB and EtxB (G33D) to ganglioside GM1: plates were coated with GM1, blocked and incubated with 1 μg/ml of either EtxB or EtxB (G33D) diluted serially (3 fold) from 1 μg/ml.
Figure 1B:
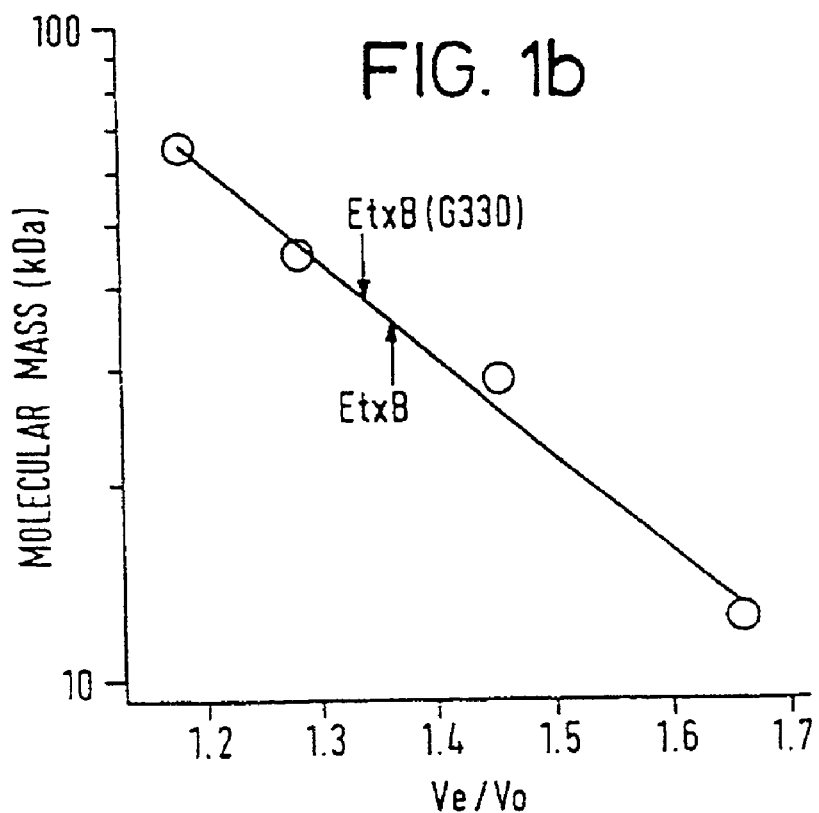

Aspects of the present invention are presented in the accompanying claims and in ration or other alteration of pre-existing condition and/or to potentially affect a future condition, as well as any combination thereof.

As used herein, the term "linked"—which is synonymous with the term "coupled"—means the linkage of the agent with the antigen—which includes but is not limited to direct linkage (such as by an ionic or covalent bond) or indirect linkage by the provision of suitable spacer groups.

As used herein, the term "not so linked"—which is synonymous with the term "uncoupled"—means that the agent is not coupled to the antigen. However, in accordance with the present invention, the agent and/or antigen can be coupled to another entity.

As used herein, the term "Ctx" refers to the cholera toxin and CtxB refers to the B subunit of the cholera toxin. In other texts, these may sometimes be identified as CT or Ct or CTB or CtB respectively.

As used herein, the term "Etx" herein means the *E. coli* heat labile enterotoxin and EtxB is the B subunit of Etx. In other texts, these may sometimes be identified as LT or Lt and LTB or LtB respectively.

As used herein, the term "administered" includes but is not limited to delivery by, a mucosal route, for example, as a nasal spray or aerosol for inhalation or as an ingestable solution; a parenteral route where delivery is by an injectable form, such as, for example, an intravenous, intramuscular or subcutaneous route.

As used herein, the term "systemic immunisation" means the introduction of an antigen into a non-mucosal tissue such as the skin or the blood.

As used herein, the term "administered" also includes but is not limited to delivery by viral or non-viral techniques. Viral delivery mechanisms include but are not limited to adenoviral vectors, adeno-associated viral (AAV) vectos, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

As used herein, the term "adjuvant" includes a substance that enhances an immune response to an antigen.

As used herein, the term "vaccine adjuvant" includes an agent which is delivered with an unrelated antigen, such that the agent is capable of facilitating an immune response to the unrelated antigen. In this way, the agent acts as a so-called vaccine adjuvant. The term "vaccine adjuvant" includes the term "mucosal adjuvant".

As used herein, the term "mucosal adjuvant" includes an agent which is delivered mucosally with an unrelated antigen, such that the agent is capable of facilitating a mucosal immune response to the unrelated antigen. In this way, the agent acts as a so-called mucosal adjuvant.

As used herein, the term "mucosal surfaces" includes but is not limited to oral, sublingual, intranasal, vaginal, rectal, salivary, intestinal and conjunctival surfaces.

As used herein, the term "mucosal membrane" and/or "mucosal tissue" includes but is not limited to the intestine, the lung, the mouth, the genital tract, the nose and the eye.

As used herein, the "vaccine carrier" includes a carrier of relevant antigens (Szostak et al 1996 J Biotechnol 44: 161-170).

It is to be appreciated that all references herein to "treatment" include one or more of curative, palliative and prophylactic treatment. In particular, the term "treatment" includes but is not limited to pre-diabetic treatment and post-diabetic treatment. By way of example, a subject in a pre-diabetic state may be treated to prevent the onset and/or progression of diabetes.

Preferably, the term treatment includes at least curative treatment and/or palliative treatment.

The treatment may be for treating conditions associated with diabetes.

As used herein, the term "diabetes" refers to a disorder in which the level of blood glucose is persistently above the normal range. Type I diabetes mellitus, the so-called juvenile type, often manifests itself in children and young adults. There is a marked failure to release insulin from the beta cells of the islets of Langerhans in the pancreas and frequently an almost complete absence of insulin in the beta cells. The only effective treatment is administration of insulin, hence the frequent designation of this form as insulin-dependent diabetes mellitus (IDDM). As used herein, the terms diabetes, Type I diabetes mellitus and IDDM are used interchangeably.

As with the term "treatment", the term "therapy" includes curative effects, alleviation effects, and prophylactic effects.

The therapy may be on humans or animals.

The therapy may be for treating conditions associated with diabetes.

Autoimmune Disease

Autoimmunity is the term used to describe the mechanism by which the body generates an immune response to self-antigens.

In accordance with a first aspect of the invention, there is provided:

(i) an agent having GM-1 binding activity, other than Ctx or Etx, or the B subunits of Ctx and Etx; or
(ii) an agent having an effect on GM-1 mediated intracellular signalling events, but no GM-1 binding activity;

for use as an agent in the treatment or the prevention of an autoimmune disease.

Agents in accordance with the present invention have been found to modulate lymphocyte populations leading to the induction of apoptosis in $CD8^+$ T cells, the enhanced activation of $CD4^+$ cells and polyclonal activation of B cells. These events are likely to shift the immune response towards induction of Th2 associated cytokines. Such responses to self or cross-reacting antigens are understood to mediate protection for certain autoimmune diseases.

In a first embodiment of this first aspect of the present invention, the agent is used in a method of treating an autoimmune disease which is in progress. In this embodiment, the agent is administered to a patient with or without co-administration of a self or cross-reacting antigen. Administration of the agent in accordance with this embodiment of the first aspect of the invention- modulates the nature of the immune response towards the self-antigen away from the activation of disease-causing inflammation and hence protects against autoimmune disease.

In a second embodiment of this first aspect of the present invention, the agent is used in a method for the "vaccination" of a mammalian subject against an autoimmune disease, in which the agent is co-administered with the self or cross-reacting antigenic determinant (or a combination of different self or cross-reacting antigenic determinants) associated with said disease. In such a manner, the subject's immune response to the self-antigen or cross-reacting antigen is switched away from the activation of pathogenesis, which therefore protects against a future autoimmune response to the self-antigen.

In this first aspect of the invention, the therapeutic agent and the self or cross-reacting antigenic determinant are, or may be, co-administered to the subject. By this we mean that the site and time of administration of each of the therapeutic agent and the antigenic determinant are such that the necessary modulation of the immune system is achieved. Thus, whilst the therapeutic agent and the antigenic determinant may be administered at the same moment in time and at the same site, there may be advantages in administering the therapeutic agent at a different time and to a different site from the antigenic determinant. Whilst single doses of the therapeutic agent and the antigenic determinant may be satisfactory, multiple doses are contemplated within the scope of this aspect of the invention.

In this second embodiment of the first aspect of the invention, the therapeutic agent and the antigenic determinant may be linked, for example covalently linked, to form a single active agent, although separate administration, in which the therapeutic agent and the antigenic determinant are not so linked is preferred because it enables separate administration of the different moieties.

Specific autoimmune diseases which may be treated in accordance with this aspect of the present invention are the autoimmune diseases where pathology is associated with cell-mediated immunity, such as rheumatoid arthritis, multiple sclerosis and diabetes.

Additionally, under this first aspect of the present invention, there is provided the use of Ctx, Etx or the B subunit of Ctx or Etx, for the manufacture of a medicament for use as an agent for the prevention of an autoimmune disease.

Also provided is a pharmaceutical composition for the treatment of a human autoimmune disease comprising (i) an agent having GM-1 binding activity; or (ii) an agent having an effect on GM-1 mediated intracellular signalling events, but no GM-1 binding activity;

and a pharmaceutically acceptable carrier or diluent therefor.

The pharmaceutical composition of this aspect of the invention may be formulated to be delivered by a mucosal route, for example as a nasal spray, or parenterally in which the composition is formulated in an injectable form, for delivery by, for example, an intravenous, intramuscular or subcutaneous route.

The pharmaceutical composition may be formulated together with the appropriate self or cross-reacting antigen. Alternatively, a kit may be provided comprising separate compositions for each of the therapeutic agent and the antigenic determinant.

Specific therapeutic agents which may be used in this aspect of the invention are EtxB and CtxB or mutants thereof retaining GM1 binding activity.

The agents for use in the first aspect of the present invention should preferably be substantially non-toxic, although some degree of toxicity may be tolerated in a severe therapy of this kind.

This first aspect of the invention extends to cover the use of all agents having GM1 binding activity, for use in the treatment of mammalian autoimmune disease, as well as those agents having an effect on GM-1 mediated intracellular signalling events, and which therefore mimic GM-1 binding agents.

Thus, this first aspect of the present invention is not limited to the use of EtxB protein as a therapeutic agent in the treatment of a human autoimmune disease. However, the use of the EtxB protein (which is a pentamer of five identical subunits) for such a treatment represents a preferred embodiment of the present invention. In addition to the wild type EtxB, this preferred aspect of the invention also extends to mutants of EtxB which have GM-1 binding activity as well as to other equivalent proteins, such as the cholera toxin B subunit (CtxB) and mutants thereof which have GM1 binding activity.

Other therapeutic agents for the treatment of autoimmune disease in accordance with the first aspect of this invention are humanised monoclonal antibodies, which bind GM1. Methods known in the art for identifying and preparing such agents are well known.

T-Lymphocyte Leukaemias

According to a second aspect of this invention, there is provided:

(i) an agent having GM-1 binding activity, other than Ctx or Etx, or the B subunits of Ctx and Etx; or (ii) an agent having an effect on GM-1 mediated intracellular signalling events, but no GM-1 binding activity;

for use in the treatment of human leukaemias of a T cell origin, such as human leukaemias of a CD8 T cell origin.

The agents for use in the second aspect of the present invention should preferably be substantially non-toxic, although some degree of toxicity may be tolerated in a severe therapy of this kind.

Additionally, under this second aspect of the present invention, there is provided the use of Ctx or Etx, or the B subunits of Ctx and Etx for the manufacture of a medicament for treatment of human leukaemias of a T cell origin, such as human leukaemias of a CD8 T cell origin.

Also provided is a pharmaceutical composition for the treatment of human leukaemias of a T cell origin comprising (i) an agent having GM-1 binding activity; or (ii) an agent having an effect on GM-1 mediated intracellular signalling events, but no GM-1 binding activity;

and a pharmaceutically acceptable carrier or diluent therefor.

The pharmaceutical composition of this aspect of the invention may be formulated to be delivered by a mucosal route, for example as a nasal spray, or parenterally in which the composition is formulated in an injectable form, for delivery by, for example, an intravenous, intramuscular or subcutaneous route.

This second aspect of the invention extends to cover the use of all agents having GM1 binding activity, for use in the treatment of human leukaemias of a T cell origin, as well as those agents having an effect on GM-1 mediated intracellular signalling events, and which therefore mimic GM-1 binding agents.

Thus, this second aspect of the present invention is not limited to the use of EtxB protein as therapeutic agents in the treatment of human T cell leukaemias. However, the use of the EtxB protein for such a treatment represents a preferred embodiment of the present invention. In addition to the wild type EtxB, this preferred aspect of the invention also extends to mutants of EtxB which have GM-1 binding activity as well as to other equivalent proteins, such as the cholera toxin B subunit (CtxB) and mutants thereof which have GM1 binding activity.

Other alternative therapeutic agents for the treatment of these diseases in accordance with this aspect of the invention are humanised monoclonal antibodies, which bind GM1. Methods known in the art for identifying and preparing such agents are well known.

Transplant Rejection and GVHD

In accordance with a third aspect of this invention, there is provided:

(i) an agent having GM-1 binding activity, other than Ctx or Etx, or the B subunits of Ctx and Etx; or (ii) an agent having an effect on GM-1 mediated intracellular signalling events, but no GM-1 binding activity;

for use as a therapeutic agent for the prevention/treatment of transplant rejection or GVHD.

Additionally, under this third aspect of the present invention, there is provided the use of Ctx or Etx or the B subunit of Etx or Ctx for the manufacture of a medicament for the prevention of transplant rejection or GVHD.

In preferred embodiments of this aspect of the invention, the therapeutic agents described may be used in the prevention of solid organ transplant rejection, either allogeneic or xenogeneic. They may also be employed in the prevention of acute graft versus host disease (GVHD), for example during bone marrow transplantation procedure.

In embodiments of this aspect of the invention where the patient is treated prior to transplantation, the therapeutic agent would be co-administered with alloantigen or xenoantigen. In embodiments in which the patient is treated after transplantation, the therapeutic agent is employed without co-administration of antigen.

In the embodiment of this aspect of the invention, where the therapeutic agent and allo-or xeno-antigenic determinant are co-administered to the subject, we mean that the site and time of administration of each of the therapeutic agent and the antigenic determinant are such that the necessary modulation of the immune system is achieved. Thus, whilst the therapeutic agent and the antigenic determinant may be administered at the same moment in time and at the same site, there may be advantages in administering the therapeutic agent at a different time and to a different site from the antigenic determinant. Furthermore, the therapeutic agent and the antigenic determinant may be covalently linked to form a single active agent, although separate administration, in which the therapeutic agent and the antigenic determinant are not so linked is preferred because it enables separate administration of the different moieties.

Whilst single doses of the therapeutic agent and the antigenic determinant may be satisfactory multiple doses are contemplated within the scope of this aspect of the invention.

In this aspect of the invention, where the agent is being used in the prevention of GVHD, the agent would normally be applied direct to the cells, for example bone marrow cells, to be transplanted.

The agent is preferably substantially non-toxic, although some degree of toxicity may be tolerated in severe therapies of this kind.

Also provided is a pharmaceutical composition for use in the treatment of transplant rejection, comprising
  (i) an agent having GM-1 binding activity; or
  (ii) an agent having an effect on GM-1 mediated intracellular signalling events, but no GM-1 binding activity;
  and a pharmaceutically acceptable carrier or diluent therefor.

The pharmaceutical composition of this aspect of the invention may be formulated to be delivered by a mucosal route, for example as a nasal spray, or parenterally in which the composition is formulated in an injectable form, for delivery by, for example, an intravenous, intramuscular or subcutaneous route.

The pharmaceutical composition may be formulated together with the appropriate allo-or xeno-antigeneic determinant. Alternatively, a kit may be provided comprising separate compositions for each of the therapeutic agent and the antigenic determinant.

This third aspect of the invention extends to cover the use of all agents having GM1 binding activity, for use in the prevention/treatment of transplant rejection or GVHD, as well as those agents having an effect on GM-1 mediated intracellular signalling events, and which therefore mimic GM-1 binding agents.

Thus, this third aspect of the invention is not limited to the use of EtxB protein as a therapeutic agent in the treatment of a transplant rejection. However, the use of the EtxB protein (which is a pentamer of five identical subunits) for such a treatment represents a preferred embodiment of the present invention. In addition to the wild type EtxB, this preferred aspect of the invention also extends to mutants of EtxB which have GM-1 binding activity as sell as to other equivalent proteins, such as the cholera toxin B subunit (CtxB) and mutants thereof which have GM1 binding activity.

Other alternative therapeutic agents for the treatment of transplant rejection in accordance with the invention are humanised monoclonal antibodies, which bind GM1. Methods known in the art for identifying and preparing such agents are well known.

Vaccination

CtxB and EtxB have already been suggested as so-called "vaccine carriers". It has now been discovered that the basis for this effect, in part, is the ability of EtxB to modulate lymphocyte populations (as discussed above) by binding to the GM-1 receptor.

Thus, in accordance with a fourth aspect of the present invention, there is provided:
  (i) an agent having GM-1 binding activity, other than Etx or Ctx or the B subunits of Etx or Ctx; or
  (ii) an agent having an effect on GM-1 mediated intracellular signalling events, but no GM-1 binding activity;
  for use in the vaccination of a mammalian subject.

The agent is capable of modulating the immune response when delivered together with an unrelated foreign antigenic determinant. Where the agent is delivered parenterally, such immunomodulation is in terms of the immune response being "directed" in a particular desired direction. Where the agent is delivered mucosally with an unrelated antigen, as a so-called "mucosal adjuvant", the agent is capable of facilitating a mucosal immune response to the unrelated antigen. The antigen and agent may be delivered together as separate moieties, or may be linked together, for example by a covalent linkage.

The agent is preferably non-toxic. In addition, where the agent is to be delivered mucosally through the gastrointestinal mucosa, it should be able to remain stable during transit through the gastrointestinal tract; for example, it should be resistant to proteolytic degradation, stable at acid pH and resistant to the detergent effects of bile.

Also provided is a pharmaceutical composition for use in the vaccination of a mammalian subject, comprising
  (i) an agent having GM-1 binding activity; or
  (ii) an agent having an effect on GM-1 mediated intracellular signalling events, but no GM-1 binding activity;
  and a pharmaceutically acceptable carrier or diluent therefor.

The pharmaceutical composition of this aspect of the invention may be formulated to be delivered by a mucosal route, for example as a nasal spray, or parenterally in which the composition is formulated in an injectable form, for delivery by, for example, an intravenous, intramuscular or subcutaneous route.

The pharmaceutical composition may be formulated together with the appropriate antigenic determinant. Alternatively, a kit may be provided comprising separate compositions for each of the therapeutic agent and the antigenic determinant.

This fourth aspect of the invention extends to cover the use of all agents having GM1 binding activity, as immunomodulators, as well as those agents having an effect on GM-1 mediated intracellular signalling events, and which therefore mimic GM-1 binding agents.

Thus, this fourth aspect of the invention is not limited to the use of EtxB protein as an immunomodulator. However, the use of the EtxB protein (which is a pentamer of five identical subunits) in such a way represents one embodiment of the present invention. In addition to the wild type EtxB, this preferred aspect of the invention also extends to mutants of EtxB which have GM-1 binding activity as well as to other equivalent proteins, such as the cholera toxin B subunit (CtxB) and mutants thereof which have GM1 binding activity.

Other alternative therapeutic agents for use as an immunomodulator in accordance with this aspect of the invention are humanised monoclonal antibodies, which bind GM1. Methods known in the art for identifying and preparing such agents are well known.

When the therapeutic agent of the invention is a protein, such as the EtxB subunit or the CtxB subunit, it may be produced, for use in all aspects of this invention, by a method in which the gene or genes coding for the specific polypeptide chain (or chains) from which the protein is formed, is inserted into a suitable vector and then used to transfect a suitable host. For example, the gene coding for the polypeptide chain from which EtxB assemble may be inserted into, for example, plasmid pMMB68, which is then used to transfect host cells, such as *Vibrio* sp.60. The protein is purified and isolated in a manner known per se.

Mutant genes expressing active mutant EtxB protein may then be produced by known methods from the wild type gene.

As previously stated, agents having GM-1 binding activity, such as specifically designed humanised monoclonal antibodies, may be designed and produced as outlined above, by methods which are known in the art.

In all aspects of the invention, the agent having GM1 binding activity may also be capable of cross-linking GM1 receptors. EtxB is one such agent which is capable of cross-linking GM1 receptors by virtue of its pentameric form.

EXAMPLES

The following examples are presented to further illustrate and explain the present invention and should not be taken as limiting in any regard.

Example 1

This example illustrates the requirement for GM-1 binding to induce differential effects on lymphocyte populations Materials and Methods Generation of a Receptor-Binding Mutant of EtxB A Gly-33 to Asp substitution was introduced into the receptor binding site of human EtxB using plasmid pTRH29, a derivative of the phagemid vector pBluescript IIKS+, that contains the genes for the A- and B-subunits of Etx (Yu, J., Webb, H. & Hirst, T. R. (1992), Molec. Microbiol. 6, 1949-1958). Mutagenesis was performed with an in vitro oligonucleotide-directed mulagenesis kit (Amersham International) using single-stranded pTRH29 as a template and a synthetic oligonucleotide (5'-TCTCTTTTATCTGCCATCG-3') (from the Microanalytical Facility, IAPGR, Cambridge Research Station, UK) as the mutagenic primer. The correct Gly to Asp substitution was confirmed by dideoxy sequencing using Sequenase II (United States Biochemical Corp.) and the resultant plasmid was designated pTRH56. The mutant etxB gene from pTRH56 was excised, using EcoRl and SpeI restriction enzymes, and inserted into pMMB68 (Sandkvist, M., Hirst, T. R. & Bagdasarian, M. (1987) J. Bacteriol. 169, 4570-4576) to yield a broad host range expression vector, pTRH64 expressing EtxB(G33D).

Antigens

Wild-type EtxB and EtxB(G33D) were purified from culture supernatants of *Vibrio* sp.60 (pMMB68) and *Vibrio* sp.60 (pTRH64), respectively, using a modification of the method reported by Amin and Hirst (Amin, T., & Hirst, T. R (1994) Prot. Express. and Purif. 5, 198-204). Briefly, proteins, were purified by diafiltration and hydrophobic interaction chromatography and concentrated by anion-exchange chromatography. The protein solutions were desalted on a PD10 column (Pharmacia, UK) equilibrated with phosphate buffered saline (PBS; 10mM sodium phosphate, 150 mM NaCl, pH7.4) and stored at −30° C.

The purity of EtxB and EtxB(G33D) were confirmed by SDS polyacrylamide gel electrophoresis. The molecular mass of the individual monomers were confirmed by laser desorption mass spectrometry (Protein Science Facility, University of Kent).

Apparent molecular masses of EtxB and EtxB(G33D) were determined by gel filtration chromatography using a SMART system (Pharmacia). Proteins were eluted from a Superdex 75 PC 3.2/30 column in PBS, pH7.5.

Irreversible denaturation of B subunit pentamers, for use in lymphocyte proliferation assays (see below), was achieved by heating the proteins at 95° C. for 5 min.

Animals, Sample Collection and Immunization Protocols

BALB/c mice (H-$2^d$; high responder to EtxB) of 7-12 weeks of age were purchased from Charles River Laboratories and maintained at the University of Kent animal house. Antibody responses to EtxB or EtxB(G33D) were measured after s.c. injection of mice with 30 g of protein in PBS, followed by boosting 10 days later. Another group of mice were given the same protein dose orally in sodium bicarbonate (50 µg/ml) on 3 occasions, and at one week intervals. Control mice were given PBS. Blood was collected 10 days following the last s.c. injection or one week following the last oral feeding. Gut secretions from live mice were isolated in a protease inhibitor solution as previously described (Elson, C. O., Ealding, W. & Lefkowitz, J. (1984) J Immunol. Meth. 67, 101-108), one week following the last feeding. Samples were then sonicated and clarified by centrifugation (13,226×g, 10 min, at 4° C.).

For the proliferative assays, mice were injected i.p. with 30 g ofEtxB or EtxB(G33D) in complete Freund's adjuvant (CFA) and the mesenteric lymph nodes isolated 10 days later. Control unimmunized mice were also included and their lymph nodes isolated in a similar manner.

Enzyme Linked Immunosorbent Assays (ELISAs)

Binding of EtxB or EtxB(G33D) to GM1 was examined by a GM1-ELISA (Amin, T., & Hirst, T. R. (1994) Prot. Express. and Purif. 5, 198-204).

Sera and gut secretions were examined for the presence of anti-B subunit IgG and IgA antibodies by ELISA's in which samples were applied to microtitre plates (Immulon I, Dynateck, USA) coated with 5 g/ml of either EtxB or EtxB (G33D) in PBS. Anti-B subunits IgA antibodies in gut secretion supernatants were extrapolated from a standard curve made by coating 2 rows of wells on each plate with 1 µg/ml rabbit anti-mouse IgA (α chain specific; Zymed Lab, USA) in PBS followed by addition of 1 µg/ml of mouse myloma IgA (MOPC 315, Sigma, USA). To measure total IgA, wells were coated with rabbit anti-mouse IgA followed by addition of gut secretion supernatants. All samples were serially diluted. Goat anti-mouse IgG (Fc fragment specific; Jackson Lab., USA) or goat anti-mouse IgA (a chain specific; Sigma) peroxidase conjugate were diluted and added to all wells. The anti-B subunit IgG titer, giving an $A_{450nm}$ of 0.2, was determined. The IgA anti-B subunit response for each of EtxB and EtxB (G33D) in gut secretions was calculated as "IgA specific activity" [mean IgA anti-B subunit (μg/ml)/total IgA (μg/ml)].

An ELISA method for measuring cytokine levels of IL-2, IL-4, IL-5, IL-10 and IFN-was used, as described previously (Harper, H. M., PhD thesis, Univeristy of Bristol (1995)). Briefly, microtiter plates were coated with rat antibodies to mouse IL-2, IL-4, IL5, IL-10 and IFN-γ. Plates were blocked with 2% (w/v) bovine serum albumin.

Supernatants from culture medium were added to wells and diluted down. One row on each plate for each cytokine contained a standard amount of recombinant cytokines. Plates were then incubated with 0.5 μg/ml of biotinylated anti-cytokine monoclonal antibodies followed by addition of avidine-peroxidase and 3,3',5,5 '-Tetramethylbenzidene (TMB) substrate and read at $A_{405nm}$.

Lymphocyte Proliferation Assay

Mice were sacrificed by cervical dislocation, mesenteric lymph nodes were excised aseptically and minced through a stainless steel mesh into Hank's balanced salt solution (HBSS) (Flow Laboratories, Irvine, Renfrewshire, UK). Cells were washed by centrifugation (500×g, 10 min, 4° C.) in HBSS and resuspended in modified Eagle's medium (Flow) to which 20 mM Hepes (Flow), 100 IU Penicillin, 100 g/ml Streptomycin, 4 mM L-glutamine (Flow) and 2-mercaptoethanol had been added (complete medium). Fresh autologous normal mouse serum from unimmunized mice was added to a final concentration of 0.5% (v/v). Cultures contained $2 \times 10^6$ viable cells/ml in either 2 ml volumes in 24-well plates or 8 ml volumes in 25 cm³ flasks (Nunc A/S, Roskide, Denmark) and were established in the presence and absence of antigens as indicated in the figures legend. Cultures were incubated at 37 μC in a humidified atmosphere of 5% $CO_2$ and 95% air for 6 days. At desired timepoints, 0.1 ml samples were removed from the cultures and transferred to 96 well U-bottomed plates (Nunc) and pulsed with 1 μCi/well of [$^3$H]-Thd (Amersham, U.K.) for 6 h before harvesting (Mach III harvesting 96 Tomtec, Orange, Conn. USA) and counting by standard liquid scintillation 1450 Micro β plus, LKB-Wallac, Turku, Finland). Similarly, 0.5 ml of supernatant was sampled from cultures for cytokine analysis. Cells were pelleted and the supernatants stored at −68° C. until analysed.

Phenotypic Analysis of Cultured Cells

Cultured cells harvested on day 4 of culture were washed and viable cells recovered at the interface of a HBSS/18% metrizamide (Nyegaard and Co., Oslo, Norway) gradient following centrifugation at 500×g for 15 min at 20° C. Cells were washed twice and resuspended in HBSS containing 0.2% sodium azide (Sigma) and 10% normal rat serum. The following rat antibodies (Pharringen, San Diego, USA) were used: fluorescein isothiocyanate (FITC) labelled anti-CD4 (RNRM4-5), FITC labelled anti-CD8 (53-6.7), biotin-labelled anti-CD25 (7D4) and Phycoerythrin (PE) labelled anti-B220 (RA3-6D2). Additionally, for the biotin-labelled antibodies Streptavidin-PE or Streptavidin-FITC (Serotech, UK) were used. All antibodies were diluted in HBSS containing azide and used at predetermined concentrations. 200 μl of $2 \times 10^6$ cells and 200 l of each the antibodies were mixed and incubated on ice for 30 min. When Streptavidin-PE or FITC secondary antibodies were required cells were incubated with these antibodies for additional 30 min. Appropriate controls for FITC and PE antibodies were also included. Cells were washed with HBSS and then analysed by 2 flow cytometry (Becton Dickinson).

Results

Generation and Characterization of a Receptor Binding Mutant of EtxB

A Gly to Asp substitution was introduced into the B subunit of E. coli heat-labile enterotoxin by oligonulceotide-directed mutagenesis of EtxB, in order to generate a mutant B subunit defective in receptor recognition. The mutant protein, designated EtxB(G33D), and wild type EtxB were purified to homogeneity (see Materials and Methods). The molecular mass of purified EtxB and EtxB(G33D) were determined by laser desorption mass spectrometry. Masses were within 20 Da of the theoretical masses of 11702 and 11760 Da for monomeric EtxB and EtxB (G33D), respectively. When analysed by SDS-PAGE without prior heating, both wild-type EtxB and EtxB(G33D) migrated as discrete stable oligomers, with apparent molecular weights of 42 kDa and 56 kDa (FIG. 1A, lane 1 and lane 2, respectively). The observed electrophoretic mobility and SDS-stability of EtxB is a characteristic property of the B subunit pentamer (see Sandkvist, M., Hirst, T. R. & Bagdasarian, M. (1987) J. Bacteriol. 169, 4570-4576). The slower electrophoretic mobility of oligomeric EtxB(G33D) is not due to a difference in the number of constituent B subunit monomers, since both pentameric EtxB and EtxB(G33D) exhibited similar retention times when analysed by high resolution gel filtration chromatography. Thus, the discrepancy in the electrophoretic mobility of the EtxB(G33D) oligomer with respect to wild-type EtxB, is likely to be due to the introduced negatively charged Asp residue causing a reduction in SDS binding and a subsequent slower migration.

EtxB and EtxB(G33D) were also compared for their stability in low pH buffers, resistance to 1.0 mg/ml of either trypsin or proteinase K, and relative reactivity towards a panel of anti-B subunit monoclonal and polyclonal antibodies. In each of these tests EtxB(G33D) exhibited identical properties to wild-type EtxB. It is therefore concluded that a Gly to Asp substitution at residue 33 in EtxB does not alter the oligomeric configuration, SDS, pH or protease stability, or antibody reactivity compared with wild-type EtxB.

Figure 1C:
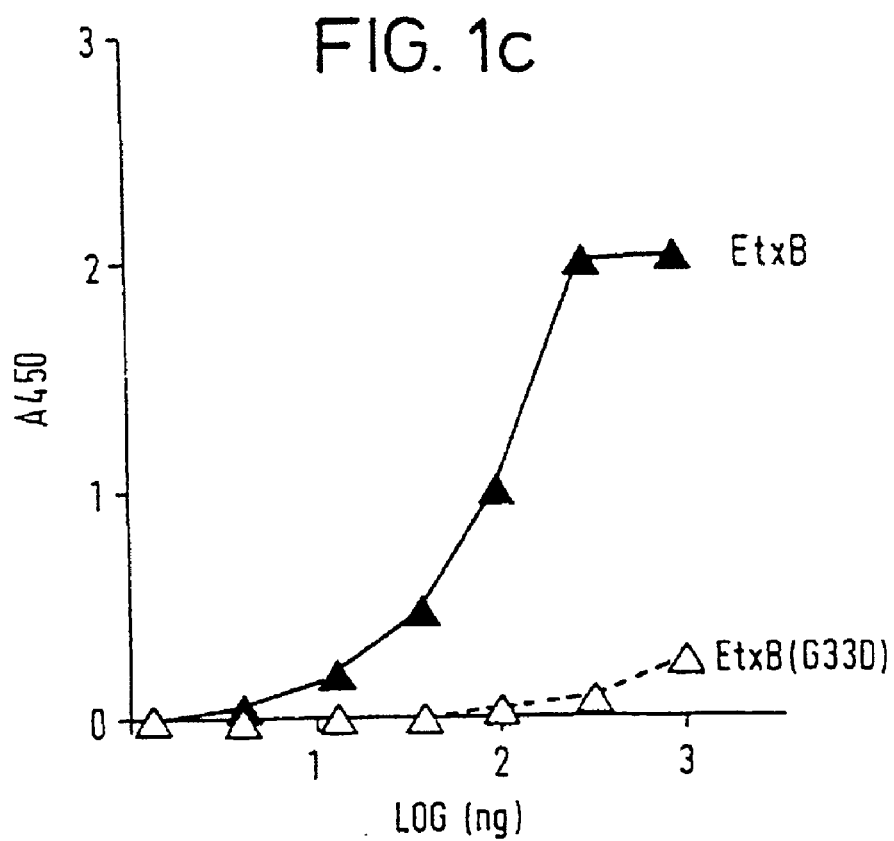

The ability of EtxB(G33D) to bind to its receptor GM1, was evaluated using a GM1-ELISA (FIG. 1C). This showed a highly significant reduction in the ability of the mutant to bind GM1 compared with the wild type protein (>99% reduction in the $A_{450nm}$ reading). Furthermore, in contrast to wild type EtxB, EtxB(G33D) failed to bind to CHO cells when examined by immunofluorescence. It is concluded that EtxB (G33D) is defective in its capacity to bind GM1 ganglioside, in vitro and in situ.

The Potent Immunogenicity of EtxB in vivo is Dependent on Receptor Binding

Figure 2:
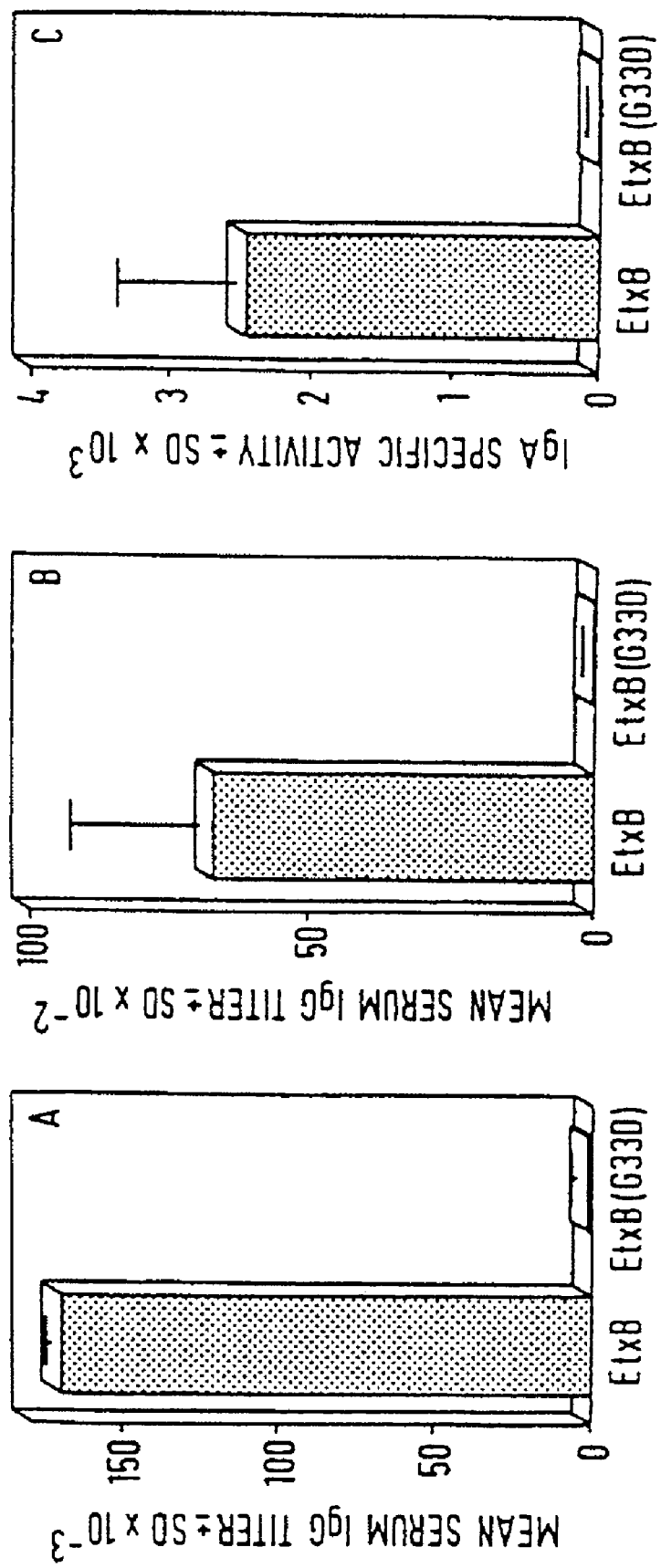
FIG. 2 illustrates that receptor binding by EtxB is essential for its potent immunogenicity in vivo. BALB/c mice (4 in each group) were either injected s.c. with EtxB or EtxB (G33D) in PBS or given the proteins orally in bicarbonate buffer. Sera were analysed 10 days following two s.c. injections (A) or 1 week following 3 oral doses (B), and gut secretions were analysed 1 week following 3 oral doses (C). No reaction was detected in samples from control mice (not shown). Results are expressed as mean IgG antibody titre in serum, while IgA in gut secretion is expressed as 'specific' activity as described below.

The importance of receptor binding in the immunogenicity of EtxB was evaluated in mice following either oral delivery or s.c. injection of EtxB or EtxB(G33D) in PBS. Oral delivery of EtxB resulted in detection of a high IgG antibody titer in serum and IgA antibody activity in gut secretions (FIG. 2). In contrast, a similar regime of oral immunization with EtxB (G33D) failed to generate any detectable antibody activity. EtxB(G33D) did induce a serum antibody response following s.c. injection, although the response was considerably lower in comparison to the antibody response to wild type EtxB, with >160 fold reduction in the mean antibody titer, 1050 versus 171000, respectively. It is concluded that receptor binding by EtxB is essential for its potent immunogenicity in vivo.

Receptor Binding Does Not Influence the Extent of Lymphocyte Proliferation in the Presence of EtxB or EtxB(G33D)

Figure 3:
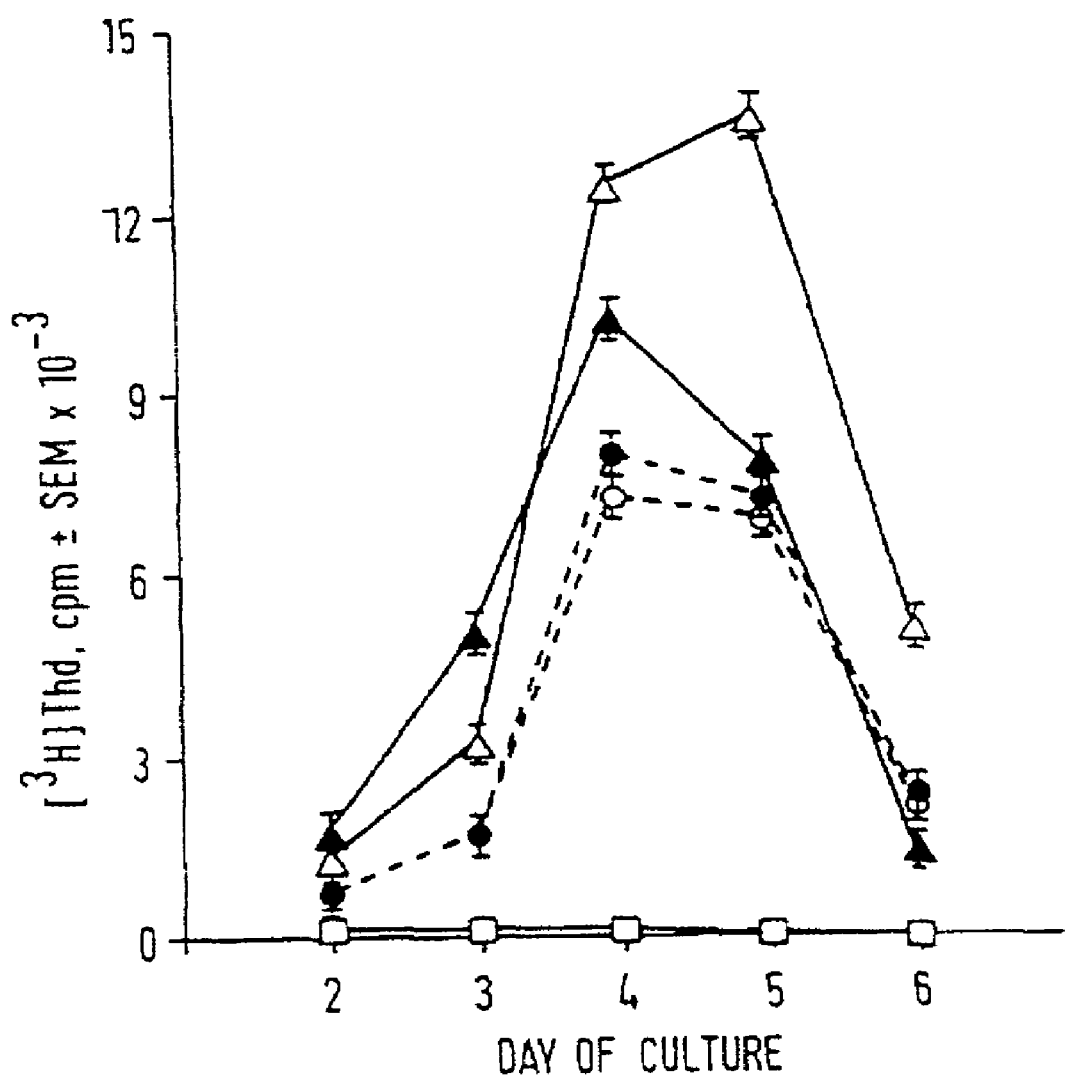
FIG. 3 illustrates the kinetics of lymphocyte proliferation. Mice were injected i.p. with 30 μg of EtxB (G33D) in complete Freund's adjuvant. MLNs were isolated 10 days later and cells were incubated in the absence of antigen (open square) or in the presence of 80 g/ml EtxB (filled triangles), EtxB (G33D) (open triangles) or their disassembled monomeric forms of EtxB (filled circles) and EtxB (G33D) (open circles) generated by heating at 95 C. The last 6 hour on each sampling day cells were pulsed with 1 μCi of ($^3$H) Thd. Data represents mean cpm and SEM of triplicate wells.

The effect of EtxB or EtxB(G33D) on lymphocyte proliferation in vitro was examined. Lymphocytes were isolated from the popliteal and mesenteric lymph nodes (MLN) of mice immunized with either EtxB or EtxB(G33D) and stimulated in vitro with either protein, or with a heat-denatured preparation of EtxB or EtxB(G33D). The proliferative response of lymphocytes derived from the popliteal or MLN was similar. In each case, proliferation to each of the protein preparations increased with increasing B subunit concentration. A representative set of data from an experiment using MLN is shown in Table 1. The magnitude of the response to wild type and mutant pentamers was comparable as was that in the presence of heat-denatured wild type and mutant monomers. FIG. 3 shows the kinetics of the proliferative responses obtained in the presence of 80 µg/ml of each of the protein preparations. Reactivity was dependent on the presence of antigen, and followed a similar pattern in the presence of each protein. Reactivity was evident on day 3 of culture with incorporation of [$^3$H]-Thd reaching a peak on day 4 and waining thereafter. The minor differences in the timing of peak responses apparent in FIG. 3 were not observed in repeat experiments, showing that the anamnestic characteristics of the responses to the EtxB and Etx(G33D) are comparable. It is concluded that the level of stimulation in the presence of the native proteins is not likely to be influenced by receptor binding or the introduced mutation.

Toxin Receptor Binding Causes Immunomodulation of B Cells and T Cell Subsets

To examine if receptor binding by EtxB exerts any effect on the populations of lymphoid cells in vitro, lymphocytes were isolated from the MLN of mice primed i.p. with EtxB(G33D) and then stimulated with either EtxB or EtxB(G33D) or a mixture of both. Additionally, a parallel experiment using MLN-derived lymphocytes from mice injected with EtxB was undertaken and resulted in essentially identical findings to those obtained from EtxB(G33D) primed mice.

(i) EtxB Causes Increased Activation of B Cells

Figure 4:
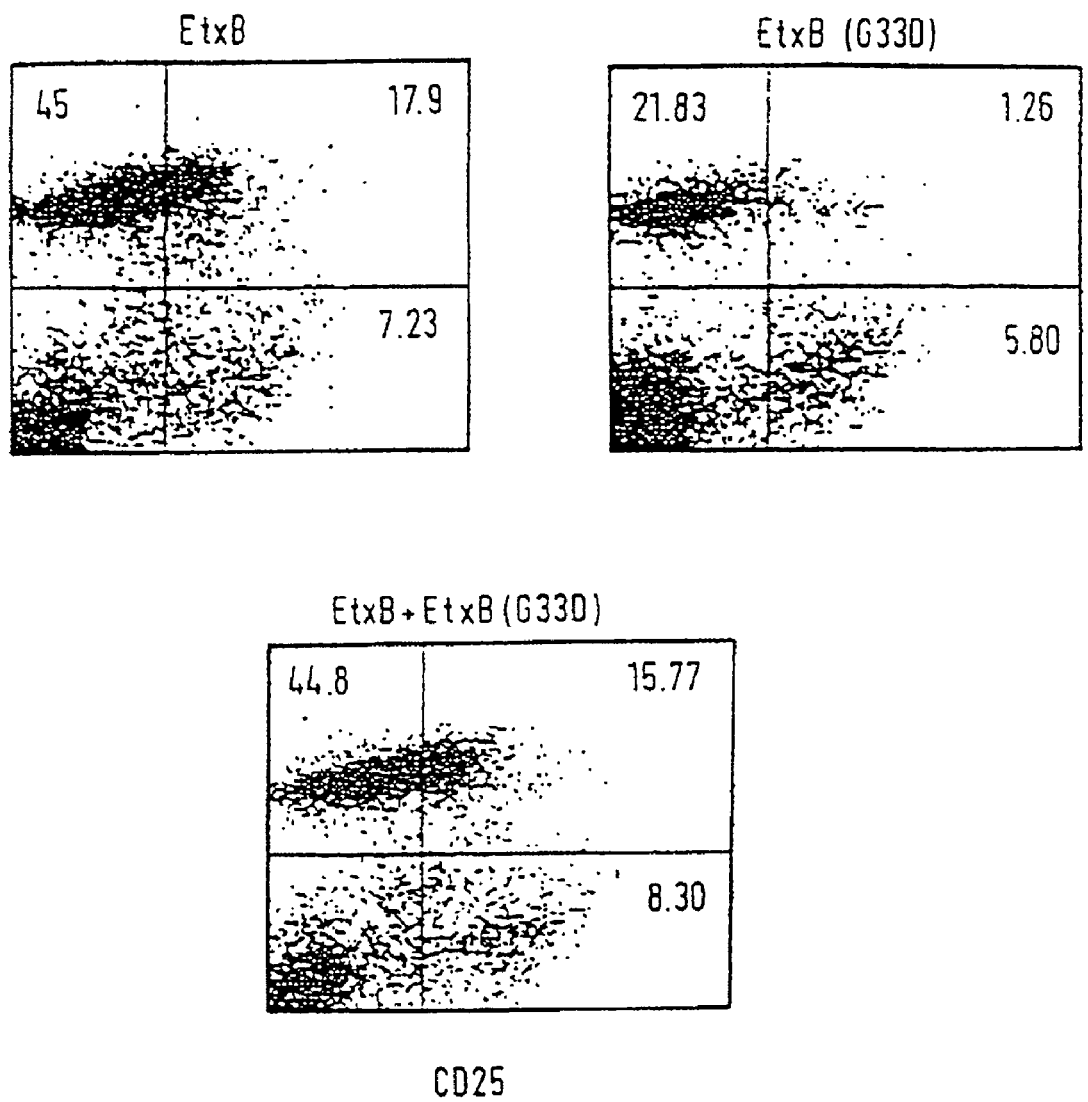
FIG. 4 illustrates that EtxB causes increased activation of 1B cells. Mice were immunized with EtxB (G33D) in CFA. Cells were isolated from mesenteric lymph nodes (MLN) 10 days later and incubated in the presence of 80 μg/ml of either EtxB or EtxB (G33D) or a mixture of 40 μg/ml of each protein. Cells were labelled with biotinylated anti-CD25 (7D4) and Phycoerythrin (PE) anti-B220 (Ra3-6D2). Streptavidin FITC was used as a secondary antibody conjugate. Controls for the antibodies were also included (not shown). Dual flow cytometric analysis was performed on day 4 of proliferation.

The effect of EtxB on B cells were examined by expression of the activation marker CD25 (IL-2Rα) in association with the B cell marker B220 (CD45R). As shown in FIG. 4 the number of B cells in cultures stimulated with EtxB was 62.9% of total cells, of which a high proportion (28.4%) expressed the cell activation marker CD25. In contrast, the proportion of B cells after stimulation in the presence of EtxB(G33D) was less than half of that of the wild type (22.26%) and fewer were activated (5.6%). To establish whether the effects exerted by EtxB were dominant, cells were incubated in the presence of an equimolar concentration of EtxB and EtxB(G33D). The flow cytometric data was similar to that obtained following stimulation in the presence of wild type EtxB alone (with 60.6% B cells, of which 26% were activated). It is concluded that the receptor binding property of EtxB mediates an increased activation of B cells in vitro.

(ii) EtxB Causes Increased Activation of CD4$^+$ T Cells and Complete Depletion of CD8$^+$ T Cells.

To examine the influence of B subunit receptor binding on T cells, lymphocytes were labelled with antibodies to CD4 or to CD8 in association with antibodies to CD25 (FIG. 5). Additionally, some cells were separately labelled with antibodies to the CD3 marker (not shown). The proportion of T cells expressing the CD4 marker when stimulated in the presence of EtxB was 36.7%, of which a high proportion (32.7%) were activated. In contrast, no detectable CD8$^+$ T cells were present in the culture containing EtxB.

By comparison, both CD4$^+$ and CD8$^+$ T cells were present in the culture stimulated in the presence of Etx3(G33D). Such cultures contained a large proportion of CD4$^+$ T cells (66.6%), but only 12% of these were activated. The proportion of CD8$^+$ T cells detected in the presence of EtxB(G33D) was 11.7% of the total number of cells, but very few of these were activated which is indicated by the absence of the CD25 marker. Additionally, in the presence of a mixture consisting of an equimolar concentration of EtxB and EtxB(G33D) the pattern of responding cells was similar to that in the presence of wild type EtxB alone; with 41.68% CD4$^+$ T cells (of which 28.6% were CD25+) and no delectable CD8$^+$ T cells (FIG. 5). In all these analyses, the proportion of cells staining with CD3 was approximately equal to the stun of those expressing CD4 and CD8 markers. These data demonstrate that the increase in activation of B and CD4$^+$ T cells and the selective depletion of CD8$^+$ T cells are mediated by toxin receptor occupancy.

Production of Cytokines

To assess whether the effect of EtxB on lymphocyte populations could be dependent on a change in cytokine production, cell cultures were incubated with either EtxB or EtxB (G33D) and supernatants removed on days 2, 3, 4, 5 and 6 for analysis. The results from samples collected on day 5 are shown in Table 2 when the maximum concentration of cytokines was detected. Both IFN-γ and IL-2 were detected in the supernatants from cultures stimulated in the presence of EtxB or EtxB(G33D), although the relative levels of these cytokines varied. The medium from cells incubated with wild type EtxB, contained a 3-fold higher concentration of IL-2 and a 1.5 fold lower level of IFN-compared with supernatants from cultures stimulated in the presence of EtxB(G33D). Despite the finding that other proliferating T cell cultures responding to other antigens yielded high levels of IL-4, IL-5 and IL-10 none of these cytokines were detected in cultures stimulated with EtxB or EtxB(-G33D). The increase in the level of IL-2 and decrease in tile level of IFN-γ following stimulation with EtxB, compared with EtxB(G33D), most likely reflects the activation status of B and CD4$^+$ T cells. Nonetheless, the results indicate that the profound effect of wild type EtxB on the CD8$^+$ T cell population is unlikely to be mediated by a major shift in the cytokine profile, as a consequence of receptor occupancy.

Discussion

These investigations show that the introduction of a single point mutation (G33D) in the receptor binding site of EtxB caused a significant loss in the ability to bind GM1. Importantly, the mutant EtxB(G33D), exhibited identical physicochemical properties to the wild type EtxB with respect to conformation, as revealed by gel chromatography, stability in SDS, acid and proteases. When the specific antibody responses were measured following immunization with either EtxB or EtxB(G33D), dramatic differences were noted. Subcutaneous injection with EtxB(G33D) in mice resulted in a highly significant drop in the antibody titer compared with wild type (ca>160 folds) while no antibody response was detected following oral administration. It is possible that these differences result from the disruption of a dominant epitope involved either in the recognition of the molecule by antibody, or the stimulation of effective T cell help for antibody production. However, it is noteworthy that the Gly to Asp substitution had no effect on the recognition of the B subunit by a panel of specific polyclonal and monoclonal antibodies. Further, the proliferative responses obtained when EtxB or EtxB(G33D) were added to cultures were comparable regardless of which of the proteins were used for in vivo priming; demonstrating that the T cell reactivity was not specific to either molecule. It is therefore concluded that receptor binding by EtxB is essential for its potent immunogenicity in vivo.

The importance of receptor binding in the potent immunogenicity of EtxB may be explained in a number of ways. Firstly, binding of the B subunit of Etx and Ctx to GM1 may increase the efficiency of uptake of these proteins, raising the local protein concentration available to the immune system. Other classes of proteins which are able to bind mucosal surfaces are found to be effective immunogens (De Aizpura, H. J., & Russell-Jones, G. J. (1988) J. Exp. Med. 167, 440-451). The observed differences in the immunogenicity of EtxB and its mutant following oral administration may indeed be due to efficient uptake of EtxB from the lumen of the gut. However, the dramatic differences noted after parenteral immunization (where antigen is delivered locally at high concentration) are suggestive of other effects. For example, binding of EtxB to GM1 may affect the efficiency of antigen presenting cell activity. Such binding could cause activation of class II-bearing cells, particularly with respect to their expression of essential co-stimulatory molecules, such as B7, which is associated with their acquiring enhanced antigen presenting activity (Jenkins, M. K. & Johnson, J. G. (1993) Curr. Opin. Immunol. 5, 361-367). Alteratively, receptor binding may have direct effects on sub-populations of lymphocytes. A number of observations from this study provide strong evidence that this is indeed the case.

The in vitro studies demonstrated that EtxB was able to induce the proliferation of primed lymph node cells. This property was not dependent on receptor binding, since responses with similar anamnestic characteristics were obtained using either wild type EtxB, EtxB(G33D) or heat-denatured monomeric forms of these proteins which cannot bind GM1. These observations are interesting in themselves since it has been widely reported that commercial preparations of Ctx and CtxB or purified recombinant CtxB are strongly inhibitory of lymphocyte proliferation in vitro. The apparent discrepancy may have arisen from the fact that previous experiments bad been conducted on purified lymphocytes and had largely used mitogen stimulated lymphocyte cultures (which are not clonally restricted responses), where a different mechanism may be involved. Consistent with this was our observation that the proliferation of Con A-stimulated lymphocytes was indeed inhibited by EtxB. However, the analyses of cell populations in cultures of primed lymph node cells stimulated with either EtxB or EtxB(G33D) revealed important differences with respect to B cells as well as CD4 and CD8-bearing T-cells.

B cells were detected after 4 days of culture in the presence of either EtxB or EtxB(G33D). However, by comparison with EtxB(G33D), the relative proportion of B cells present in cultures with EtxB %%as increased by approximately 100%. This increase was associated with the expression of CD25 on a very high proportion of the B cells. In the experiment shown, the responding lymphocytes were primed with EtxB (G33D) in vivo. Similar experiments with cells from EtxB immunized mice revealed comparable results. Thus, irrespective of any in vivo effects associated with receptor binding, cultures in the presence of EtxB contained a larger proportion of B cells compared with those stimulated with EtxB(G33D). These effects on B cells also appear not to be dependent, at least in part, on regulation by. T cells, in vitro, as the results do not suggest a major shift in the profile of the detected cytokines. Therefore, in vitro, receptor binding by EtxB appears to be associated with a direct effect on B cells, resulting in proportional expansion of this population as well as their activation. It is also noteworthy that CtxB has been shown to increase expression of MHC class II on virgin B cells, a property which was not exhibited by a GM1 binding mutant CtxB (G33E) (Francis, M. L., Ryan, J., Jobling, M. G., Holmes R. K., Moss, J, & Mond J. J. (1992) J. Immmunol. 148, 1999-2005). The results in these experiments suggest the presence of direct mitogenic effects by EtxB on antigen-primed B cells and demonstrate that such effects are mediated by receptor binding.

In addition to the effects of EtxB on B cells in culture, flow cytometric analyses reveal that this toxoid caused the complete depletion of any detectable $CD8^+$ cells. Once again, this effect was shown to be dependent on receptor binding, since this population of T cells were not depleted in cultures containing EtxB(G33D). Further, complete depletion of $CD8^+$ cells in cultures containing EtxB was observed, from mice immunized with wild type EtxB. There are three possible mechanisms by which such an effect may be mediated. 1) It is known that binding of Ctx or CtxB to GM1 on rat MLN cells induces patch and cap formation (Craig S. W. and Cuatrecasas P., (1975) Proc. Natl. Acad. Sci. USA, Vol.72, pages 3844-3848). It is possible that in this process EtxB-GM1 complexes and other molecules, including CD8, are internalized. Such a process would prevent flow cytometric detection of these cells using CD8 as a marker, and may result in their death due to the associated loss of the surface TCR complex. Although the latter may account for the absence of $CD8^+$ T cells in the culture, others found no loss of the TCR complex from the surface of human Jarkat T cell line when CtxB was used (Imboden, J. B., Shoback, D. M., Pattison, G, & Stobo, J. D. (1986) Proc. Natl. Acad. Sci. USA 83, 5673-5677). Absence of effects as a result of capping is supported by the finding that CD3 and CD4 markers were not affected. 2) An alterative mechanism would involve effects exerted by cytokines in culture. In this study, both IL-2 and IFN-were detected. The results, however do not suggest a major shift in the cytokine profile which would explain such a dramatic effect on $CD8^+$ T cells. 3) Absence of $CD8^+$ T cells may be due to active induction of apoptosis. Death of lymphocytes by apoptosis may involve capping as described above, or could be mediated in the absence of capping by effects on the signalling events in the cell. Activation-induced programmed death is dependent on $Ca^{2+}$ and involves phosphatases and kinases. Binding of CtxB to lymphocytes has been shown to inhibit protein kinase C-dependent proliferation and induced a pronounced increase in intra-cellular $Ca^{2+}$, events which were not associated with an increase in CAMP level. The ability of EtxB to deplete CD8+, but not CD4+ T cells could be due to differential effects of signals associated with the CD4/CD8-TCR complex, resulting from crosslinking GM1 on the surface of these subset of lymphocytes. This could be as a result of differential binding of the toxoid on the membrane as reported for CtxB or alternatively to the differential signalling mechanisms in $CD4^+$ and $CD8^+$ T cells.

In the complete absence of detectable $CD8^+$ T cells, EtxB increased the proportion of $CD4^+$ T cells which were activated, by comparison with the receptor binding mutant. The essential requirement for $CD4^+$ T cells in response to Ctx has been demonstrated in vivo. The reason for the increased activation of this T cell subset is, however, unclear. It is noteworthy that CtxB has been shown to stimulate DNA synthesis and cell division in quiescent non-transformed mouse 3T3 cells. A selective mitogenic effect on $CD4^+$ T cells was also found in the presence of plant lectins which bind to Galβ-1-3-3Gal-NAc, the same component that EtxB binds to in GM1. The possibility can not be ruled out that EtxB mediates a GM1-binding dependent direct effect on $CD4^+$ T cells, causing their activation. However, it is also possible that the increased activation of CD4+ T cells in cultures containing EtxB is a consequence of those changes to the B cell and CD8+ T cells populations described. B cell activation is known to be associated with an enhancement of their competency as antigen presenting cells for CD4+ T cells. Further, CD8+ T cells are widely associated with a regulatory role in immune reactivity both in vivo and in vitro.

Their removal from T cell proliferative cultures has been associated with prolonged and enhanced levels of CD4+ T cell division.

Taken together, the potent immunogenicity of EtxB in vivo, as shown in this study, can be suggested to occur as a result of its ability to increase activation of B cells exerted by growth regulating effects following binding to GM1. Activation of CD4+ T cells and the ability of EtxB to increase production of IL-2 in culture in vitro may provide the necessary signal for further expansion of B cell clones. Depletion of CD8+ T cells by EtxB in vitro in this study may also provide another mechanism of immunopotentiation in vivo following systemic or oral delivery, particularly in the light of the involvement of this subset of cells in suppression of the immune response and in oral tolerance. In this regard, both Ctx and Etx have been shown to abrogate oral tolerance to cofed soluble proteins and other studies implicated Ctx and CtxB depletion effects on intra-epithelial lymphocytes in the gut or in the dome of Peyer's patch to explain this mechanism. CtxB-inhibitory effects on CD8+T cells in vitro has also been shown to prevent graft versus host reaction.

In conclusion, it has been demonstrated that the presence of potent immunomodulatory effects by EtxB on the antibody response in vivo, and on populations of lymphocytes in vitro. Furthermore, it has been demonstrated that these effects are mediated by receptor binding. Our findings are also pertinent to an understanding of the ability of Etx and Ctx to act as potent adjuvants and as potential protein carriers for other antigens and suggest that such properties rely on the capacity of these toxoids to bind ganglioside receptors on the surface of lymphoid cells.

Example 2

This example illustrates that the effects on CD8 cells are irrespective of antigen recognition and are mediated by apoptosis.

Recombinant preparations of EtxB and EtxB(G33D) were prepared as in Example 1. Both proteins were well characterised with respect to binding to GM1, binding to a panel of monoclonal and polyclonal antibodies and various other physico-chemical properties.

Ovalbumin (OVA) was purchased from Sigma (Poole, UK). Mesenteric lymph nodes (MLN) were isolated from BALB/c mice (high responder strain to EtxB (Nashar, T. O. and Hirst, T. R. 1995. Immunoregulatory role of H-2 and intra-H-2 alleles on antibody responses to recombinant preparations of B-subunits of *Escherichia coli* heat-labile enterotoxin (rEtxB) and cholera toxin (rCtxB). *Vaccine* 13:803.)] 8-10 weeks old. Mice were injected i.p. with 200 g of OVA (Sigma) emulsified in incomplete Freund s adjuvant (Sigma). MLN were removed 10 days after injection, minced through a stainless steel mesh into HBSS (Flow, Irvine, UK). The recovered cells were washed in HBSS by centrifugation (500 g, 10 min, 4° C.) and resuspended in modified Eagle s medium (Flow) containing 20 mM HEPES, 100 IU penicillin, 100 μg/ml streptomycin, 4 mM L-glutamine and $5\times10^{-5}$ M 2-mercaptoethanol (complete medium) to which 0.5% (v/v) of Fresh autologous mouse serum was added. Cultures contained $2\times10^6$ viable cells/ml in 2 ml volumes in 24-well plates Nunc, Roskide, Denmark) and were established in the presence of 100 μg/ml OVA (dialysed extensively- in complete medium), either alone or with 40 g/ml of EtxB or EtxB (G33D). Cultures were incubated at 37 C in 5% $CO_2$and 95% air for 5 days. At desired time points, 0.1 ml samples were removed from the cultures and transferred to 96 well U-bottomed plates (Nunc) and pulsed with 1 Ci/well of [$^3$H]thymidine (Amersham, UK) for 6 h before harvesting (Mach III harvesting 96; Tomtec, Orange, Conn.) and counting by standard liquid scintillation (1450 Micro b plus; LKB-Wallac, Turku, Finland). For flow cytometric analysis (Becton Dickinson, Erenbodegem-Aalst, Belgium) of T cells, cells were stained with the following rat antibodies (PharMingen, Cambridge, U)K): FITC labelled anti-CD4 (RNRM4-5) or FITC-anti-CD8α (53-6.7) and with biotin-labelled anti-CD25 (IL-2Rα) (7D4) followed by Streptavidin-phycoerythrin. Additionally, for the biotin-labelled antibodies FITC-labelled Streptavidin was used. FACS analysis of recovered cells was performed on the peak day of proliferation (day 4), as determined by [$^3$H]thymidine incorporation.

For apoptosis assays, fresh MLN cells (MLNC) and splenic T cells (SPLTC) were isolated from BALB/c mice, 8-10 weeks old. MLNC comprising >90% $CD3^+$ T cells, as determined by flow cytometric analysis, were incubated for 2 h in petri dishes (Costar, Cambridge, Mass.) in complete medium containing 10% FCS, at 37° C. in 5% $CO_2$ and 95% air to remove adherent cells. The non-adherent fraction was subsequently pipetted off, pelleted and washed twice in HBSS before use. SPLTC were purified by negative selection using glass beads coated with normal mouse serum followed by rabbit anti-mouse γ-globulins as described (Wigzell, H. 1976. Specific affinity fractionation of lymphocytes using glass or plastic bead columns. *Scand. J. Immunol.* 5:(suppl.5) 23.). The selected population of T cells were >90% $CD3^+$ as determined by flow cytometric analysis.

$CD4^+$ and $CD8^+$ T cells were separated as follows: non-adherent MLNC were labelled with rat phycoerythrin-anti-mouse CD4 (4708-02) or FITC-anti-mouse CD8 (53-6.7) (PharMingen) and were then incubated with MACS colloidal super-paramagnetic microbeads conjugated with goat anti-rat IgG (H+L) F(ab')$_2$ (PharMingen), according to the manufacturer s instructions. These were applied to mini-MACS columns (Miltenyi Biotec, Bergisch Gladbach, Germany) in order to separate both positively (>99% pure) and negatively (>90% pure) selected populations of CD4 and CD8+ T cells, as determined by flow cytometric analysis.

Two methods were used for quantification of apoptosis: i) staining DNA with acridine orange to examine nuclear morphology and, ii) cell cycle analysis following staining DNA with propidium iodide and with either anti-CD4 or anti-CD8 antibodies. Cultures of $2\times10^6$/ml MLNC, SPLTC and fractionated MLNC were established in complete medium containing 10% FCS, in the absence or presence of 80 μg/ml of either EtxB or rEtxB(G33D) and examined from 4 to 18 h. Following incubation, cells were pelleted, washed with HBSS and stained with 5 g/ml acridine orange (Sigma). Thymocytes were isolated and treated in the absence or in the presence of $10^{-7}$M dexamethasone and used as a positive control for cells undergoing apoptosis. Nuclear morphological changes in lymphocytes were examined by conventional or confocal fluorescence microscopy (Leica TCS 4D). The proportion of $CD4^+$ and $CD8^+$ SPLTC in the sub-$G_0$/$G_1$ stage of the cell cycle was determined by flow cytometric analysis of the DNA content following staining with propidium iodide as described (O'Connor, P. M., Jackman, J., Jondle, D., Bhatia, K., Magrath, I. and Kohn, K. W. 1993. Role of p53 tumor suppressor gene in cell cycle arrest and radiosensitivity of Burkitt's lymphoma cell lines. *Cancer. Res.* 53:4776.). Cells isolated from 18 h cultures of SPLTC incubated alone or with 40 g/ml EtxB or EtxB(G33D) were stained with FITC rat anti-CD4 or FITC-anti-CD8α. Stained cells were adjusted to $1 \times 10^6$/ml in cold HBSS containing 20 mM HEPES and 0.5 mM EDTA and were fixed with cold ethanol added dropwise. Then, 50 g/ml propidium iodide and 40 g/ml ribonuclease A (DNase free) were added, and the cells incubated for 1 h at room temperature. The relative intensity of DNA staining with propidium iodide in CD4 and $CD8^+$ T cells was determined by gating on cells co-stained with each mAB.

Figure 6:
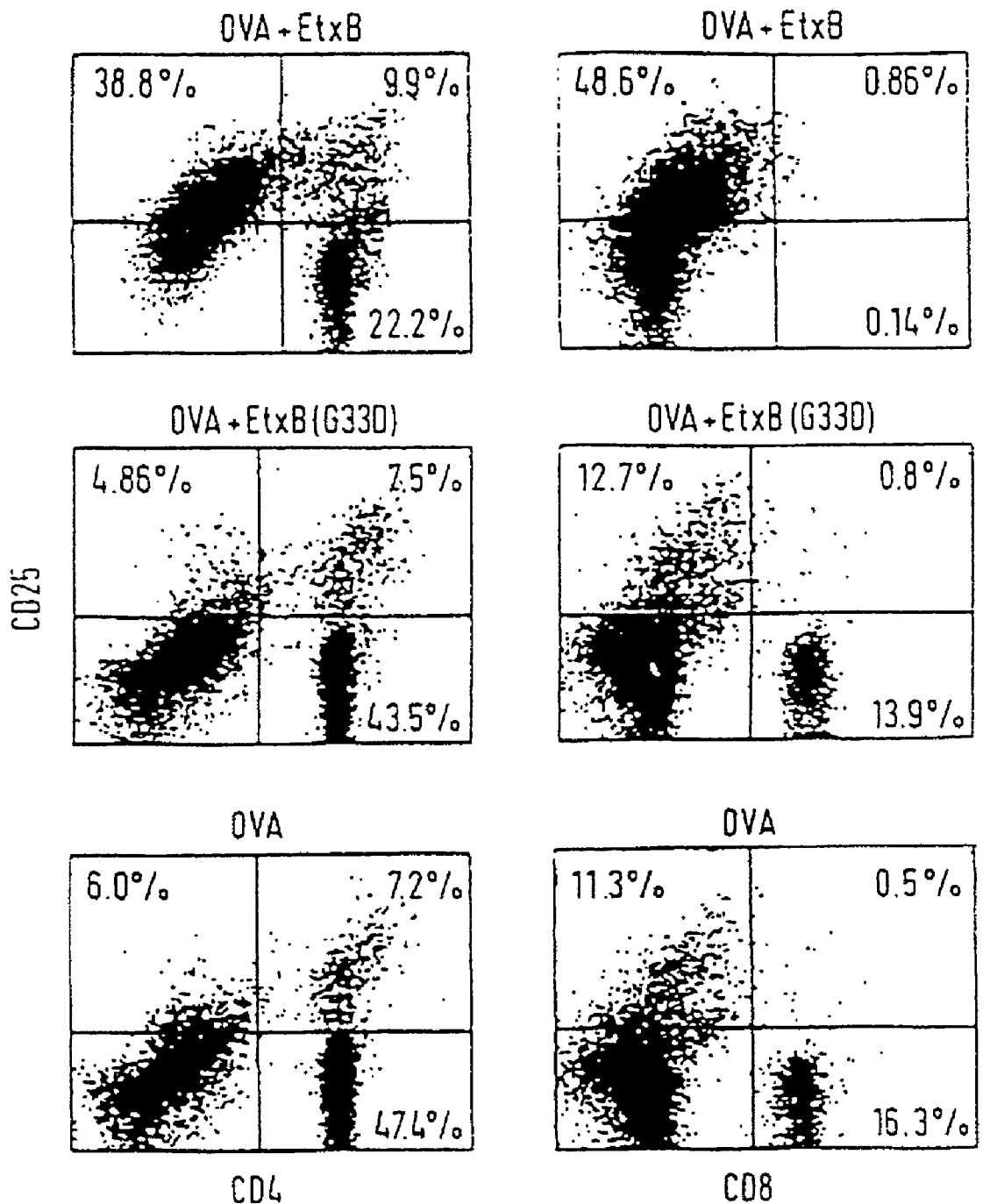
FIG. 6 shows the selective depletion of OVA-responsive CD8$^+$ T cells by EtxB. Cultures of cells from MLN taken from OVA-primed mice were established for 5 days, in the absence of antigen or in the presence of OVA+EtxB, OVA+EtxB(G33D) or OVA alone at 100 μg OVA and 40 μg/ml each of EtxB or EtxB(G33D) or 100 μg OVA alone. Cells were labelled with the following rat antibodies: FITC-anti-CD4 or FITC-anti-CD8 and both with biotin-anti-CD25 (IL-2Rα) followed by Streptavidin-phycoerythrin. Non-stained cells or cells stained with the second antibody alone were also included as controls. Cells were analysed by FACS (Becton Dickinson). The higher increase in the proportion of total cells which are CD25+ in cultures containing EtxB compared with other treatments is due to the presence of higher proportion of B cells expressing this marker (not shown). The scale of fluorescence intensity is log.

In Example 1, the observation that $CD8^+$ T cells are completely depleted from cultures of lymph node cells proliferating in response to EtxB suggested that EtxB exerts a polyclonal effect on this T cell subset. To investigate whether such effects are dependent on the activation of EtxB responsive cells, cultures were established from OVA-primed mice and stimulated with OVA alone or with OVA plus either EtxB or the mutant EtxB(G33D). Similar peak levels of proliferation (day 4 of culture in each case) were achieved in the presence of OVA alone, OVA plus EtxB or OVA plus EtxB(G33D) (9734±347, 12,031±135 and 9305±290 c.p.m. respectively). However, there was a dramatic difference in the distribution of T cell subsets in these cultures after 4 days (FIG. 6). All cultures contained $CD4^+$ T cells of which similar proportions co-expressed the activation marker CD25. However, $CD8^+$ T cells were undetectable in cultures incubated with OVA plus EtxB, but were clearly present (although not activated as assessed by CD25 expression) in cultures with OVA plus EtxB(G33D) or OVA alone. This establishes that EtxB induces depletion of $CD8^+$ T cells responding to an antigen other than EtxB. Moreover, the absence of such a response to EtxB(G33D) indicates that depletion is triggered following toxoid receptor interaction. It was also noted that the presence of wild-type EtxB caused a significant increase in the proportion of B cells of which a large number were $CD25^+$ (not shown) as had previously been found for EtxB responsive cultures (Example 1). It is therefore concluded that receptor occupancy by EtxB exerts profound immunomodulatory effects on lymphocytes irrespective of their antigen specificity.

The possibility that CD8+ T cells undergo apoptosis when cultured in the presence of EtxB was investigated. MLNC or purified SPLTC, from unprimed mice, were incubated with EtxB or EtxB(G33D) and changes in cell nuclear morphology after staining with acridine orange were recorded over a period of 4 to 18 b (Table 3 and FIG. 7). Cell morphological changes were characterized by the presence of condensation of chromatin resulting in the lobular appearance of the nucleus (FIG. 7). Other cell features such as blebbing of the plasma membrane and the presence of apoptotic bodies were also observed. These morphological changes occurred in approximately one third of each of the cell preparations treated with EtxB, whereas a much lower incidence was observed in cells cultured with EtxB(G33D) or without exogenous antigen (Table 3). Since $CD8^+$ T cells accounted for ~35-40% of the MLNC and SPLTC preparations, depletion of these cells could account for the observed apoptosis. To establish if this was the case, populations of purified CD8 and $CD4^+$ T cells were cultured for 18 h in the presence of antigens (Table 3). Similar percentages of morphological changes were induced in negatively selected populations of $CD4^+$ T cells (containing >90% CD4-bearing cells) on treatment with either EtxB, EtxB(G33D) or no antigen, indicating that binding of EtxB to its receptor does not trigger apoptosis in this T cell subset. In contrast, >70% of the negatively selected $CD8^+$ T cells (>90% pure) exhibited morphological changes when cultured with wild-type EtxB; while incubation with either no antigen or EtxB(G33D) caused changes in only 11-19% of this T cell population, respectively. Further, the presence of low numbers of contaminating cells in the purified populations used (~10% in each case) could not account for the observed effects since more highly purified populations containing >99% of CD8 or $CD4^+$ T-cells (isolated by positive selection) responded to EtxB in a similar manner (60% were apoptotic in the presence of EtxB, compared with 7% for both no antigen and EtxB(G33D) treatments) (Table 3). Apoptosis was detected in 40% and 98% of thynocytes after 18 h incubation in the absence or in the presence of dexamethasone respectively.

Figure 8:
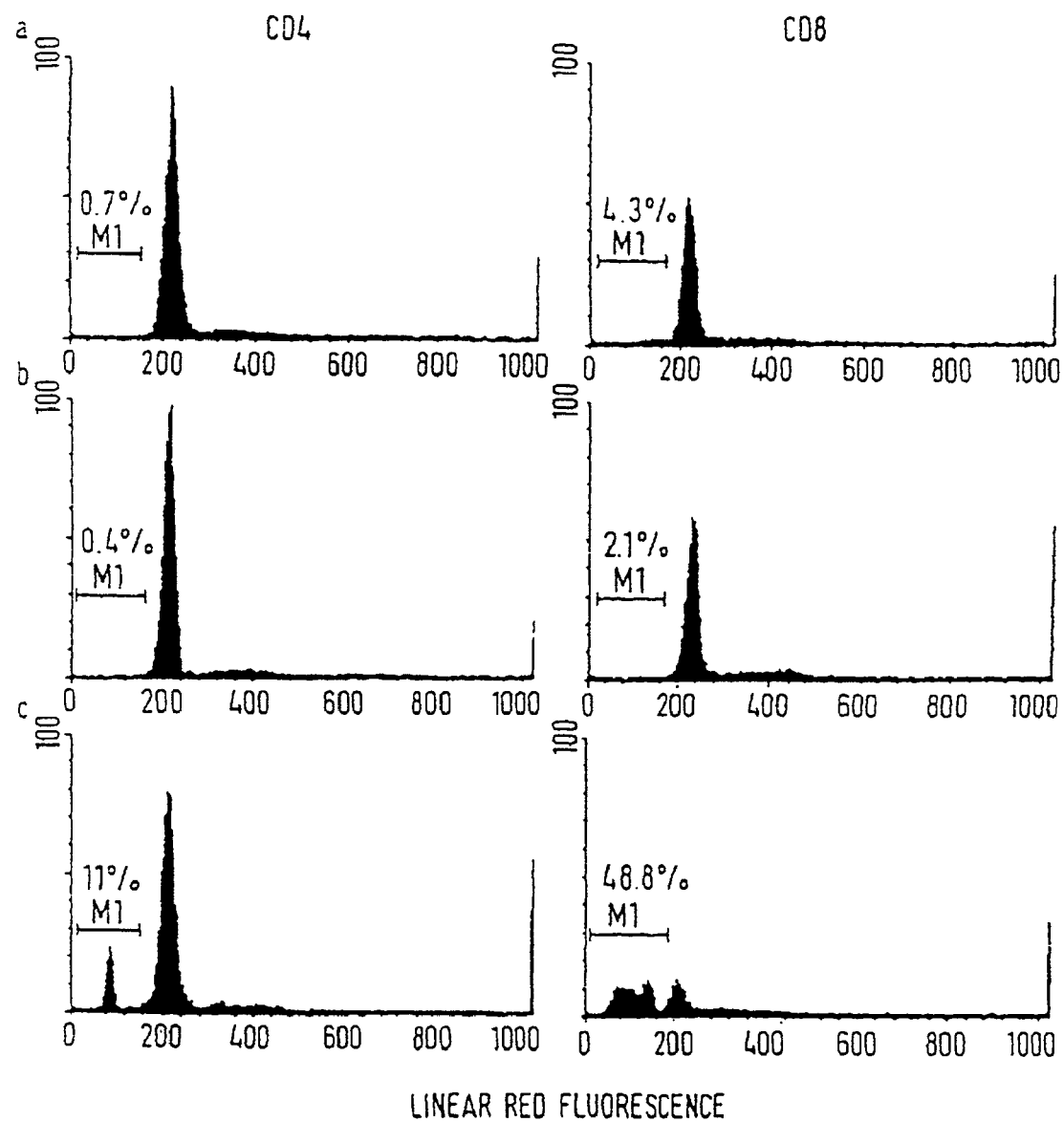
FIG. 8 shows EtxB receptor-mediated apoptosis of CD8$^+$ T cells as measured by cell cycle analysis. The proportion of CD4$^+$ and CD8$^+$ SPLTC in the sub-$G_0/G_1$ stage of the cell cycle was determined by flow cytometric analysis of the DNA content following staining with propidium iodide. SPLTC were isolated from the spleen by negative selection as described above. The cells were treated for 18 h with: (a) no antigen, (b) 80 μg/ml EtxB(G33D) or (c) 80 μg/ml EtxB and then stained with FITC-rat anti-CD4 or FITC-rat anti-CD8α. The cells were subsequently stained with propidium iodide. The proportion of cells co-stained with propidium iodide was determined by gating on cells stained with either anti-CD4 or anti-CD8 antibodies. This experiment has been carried out on cells, results of which are also reported in FIG. 7 and Table 3.

To demonstrate that the morphological changes observed in our cultures were consistent with the induction of apoptosis, the appearance of subdiploid DNA in cultures of SPLTC treated for 18 h with EtxB was evaluated. Cells were subjected to flow cytomeric analysis after co-staining with propidium iodide and either anti-CD8 or anti-CD4 antibodies (FIG. 8). Approximately 48% of the $CD8^+$ T cells from cultures incubated with EtxB fell below the diploid $G_0/G_1$ peak of propidium iodide staining, indicating that they were undergoing apoptosis (O'Connor, P. M. et al, supra). A small proportion of cells expressing CD4, in cultures with EtxB, also exhibited sub-$G_0/G_1$ levels of DNA (~11%; which may result from the death of such a high proportion of $CD8^+$ T cells). In contrast, the majority of CD4 or $CD8^+$ T cells cultured without antigen or in the presence of EtxB(G33D) were in $G_0/G_1$ phase of the cell cycle, with <5% exhibiting apoptosis. We conclude that the observed nuclear morphological changes, and the presence of sub-$G_0/G_1$ levels of DNA, in a substantial proportion of $CD8^+$ T cells treated with EtxB demonstrate a selective apoptosis triggered by the cholera-like enterotoxoid. The failure of the receptor binding mutant, EtxB(G33D), to induce similar effects demonstrates that the induction of $CD8^+$ T cell apoptosis is linked to its ability to bind to GM1 ganglioside.

Example 3

Groups of 8 male DBA/1 mice were either unchallenged (group A) or were each injected with 100 g of bovine collagen in CFA on day 0 byintra-dermal (i.d.) injection into the flank. Collagen injected mice were either left unprotected (group B; positive control) or attempts were made to prevent disease development by the administration i.d. at an adjacent site to collagen challenge of; 100 g ofEtxB in IFA on day 0 (group C), 100 g of EtxB in IFA on day 14 (group D), or 100 g EtxB(G33D) in IFA on day 0 (group E). All animals, except those in group A, received a boosting dose of collagen in IFA i.d. on day 21, and disease severity was assessed on day 45 by measuring hind limb ankle thickness (experiment A) or scoring each hind limb digit for swelling (scale 0-3 where 0=normal, and 3=maximal swelling; experiment B).

Figure 9B:
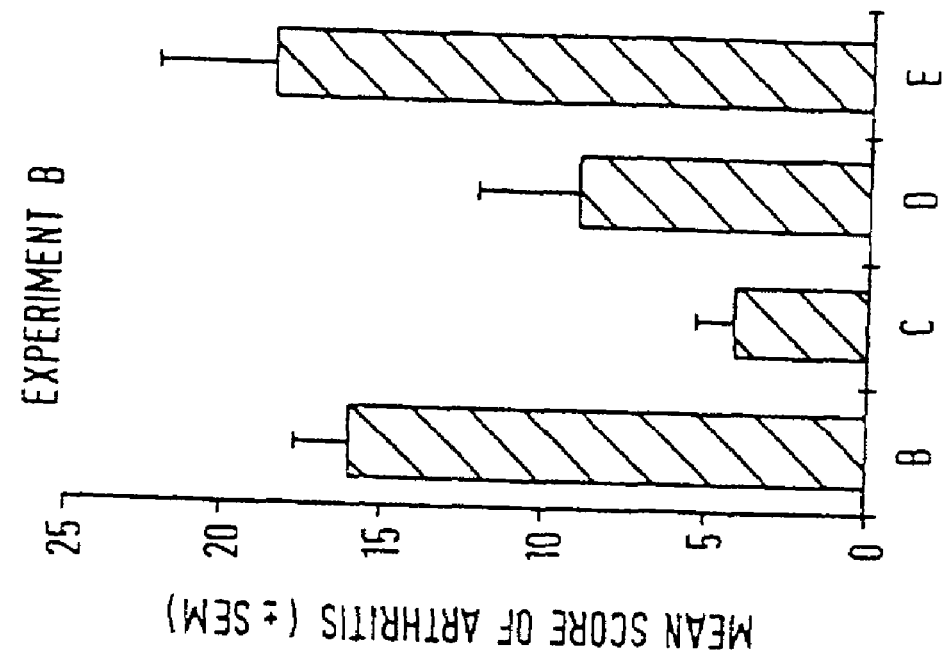
FIGS. 9a and 9b show the results of experiments conducted to show that GM-1 binding by EtxB inhibits the development of collagen induced arthritis in an animal model.
Figure 9A:
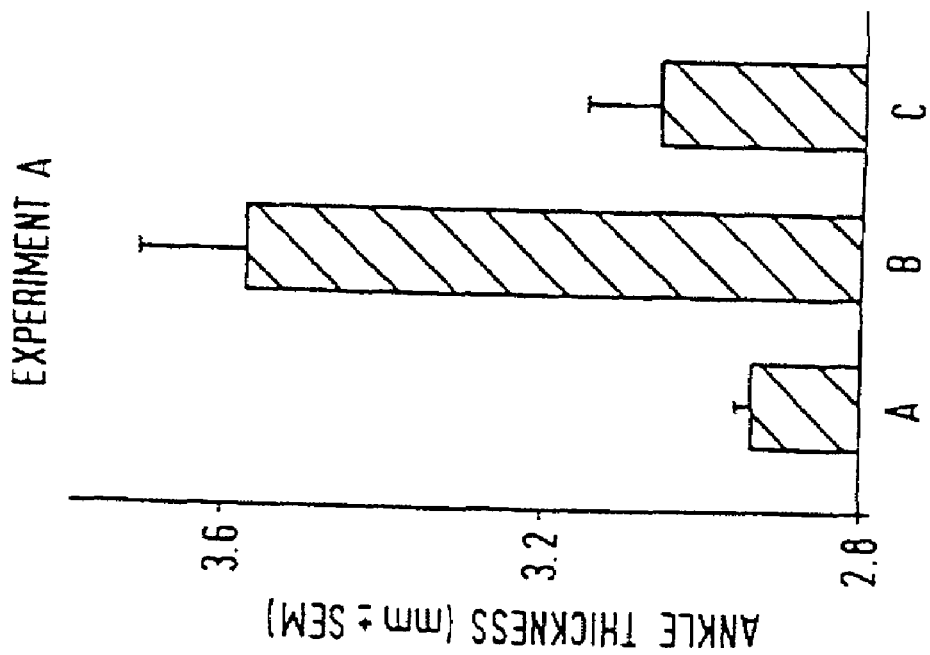
Figure 12:
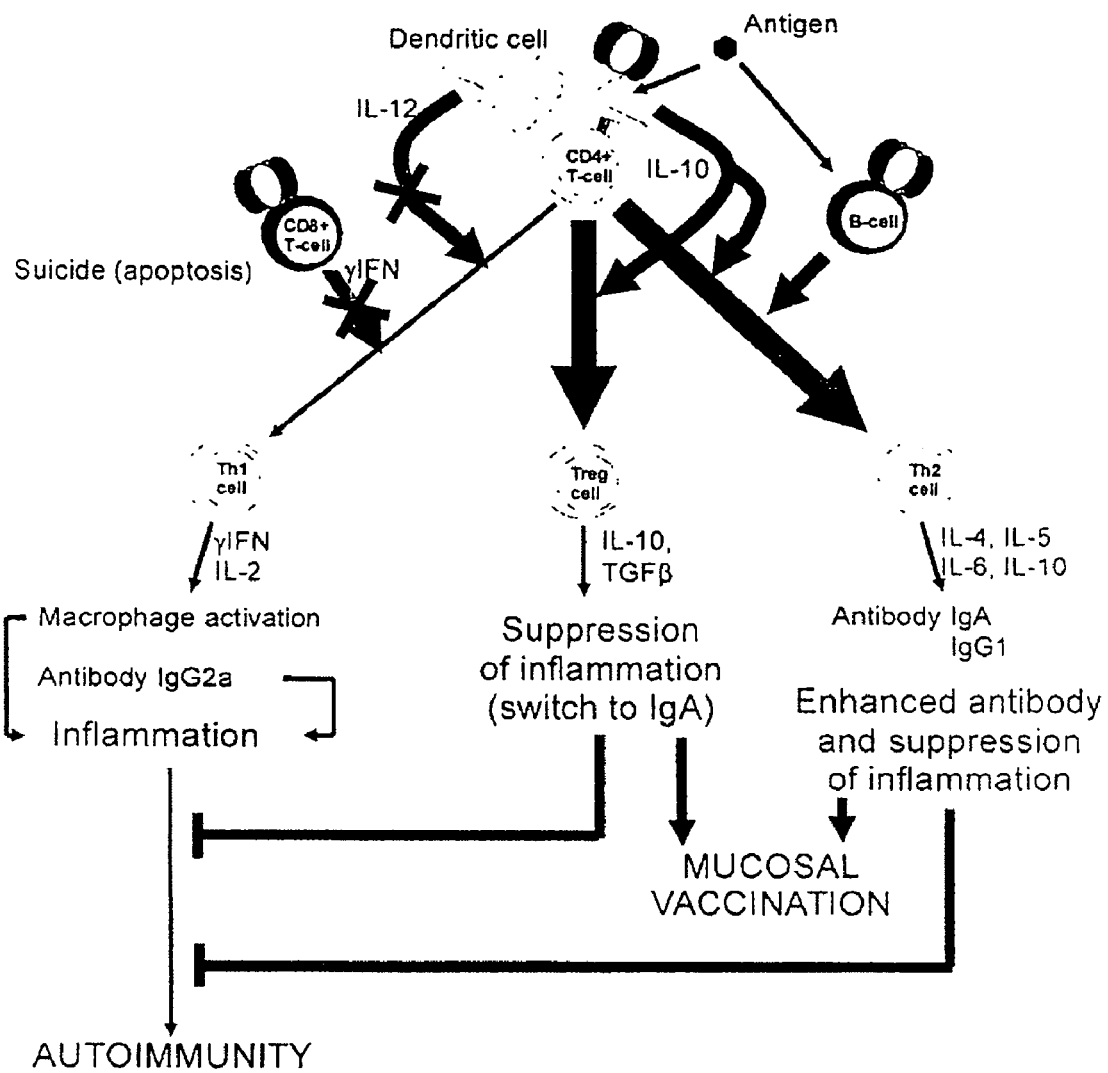
FIG. 12 shows the mechanism of action of EtxB. By interacting with a number of cells critical in the development of the immune response, EtxB is able to alter the nature of the response. The induction of apoptosis in CD8+ T-cells, and the suppression of IL-12 production by antigen presenting cells inhibit the activation of pro-inflammtory responses. The induction of IL-10 secretion by antigen presenting cells and the activation of B-cells promotes the differentiation of T-cells to Th2 and T regulatory cells. Both cell types contribute to the suppression of the Th1 response. Th2 cells promote the production of non-complement fixing antibodies and mucosal IgA, the latter may be further aided by T-regulatory cell production of TGF. Importantly, EtxB does not stimulate the production of Th2 associated IgE.
Figure 13:
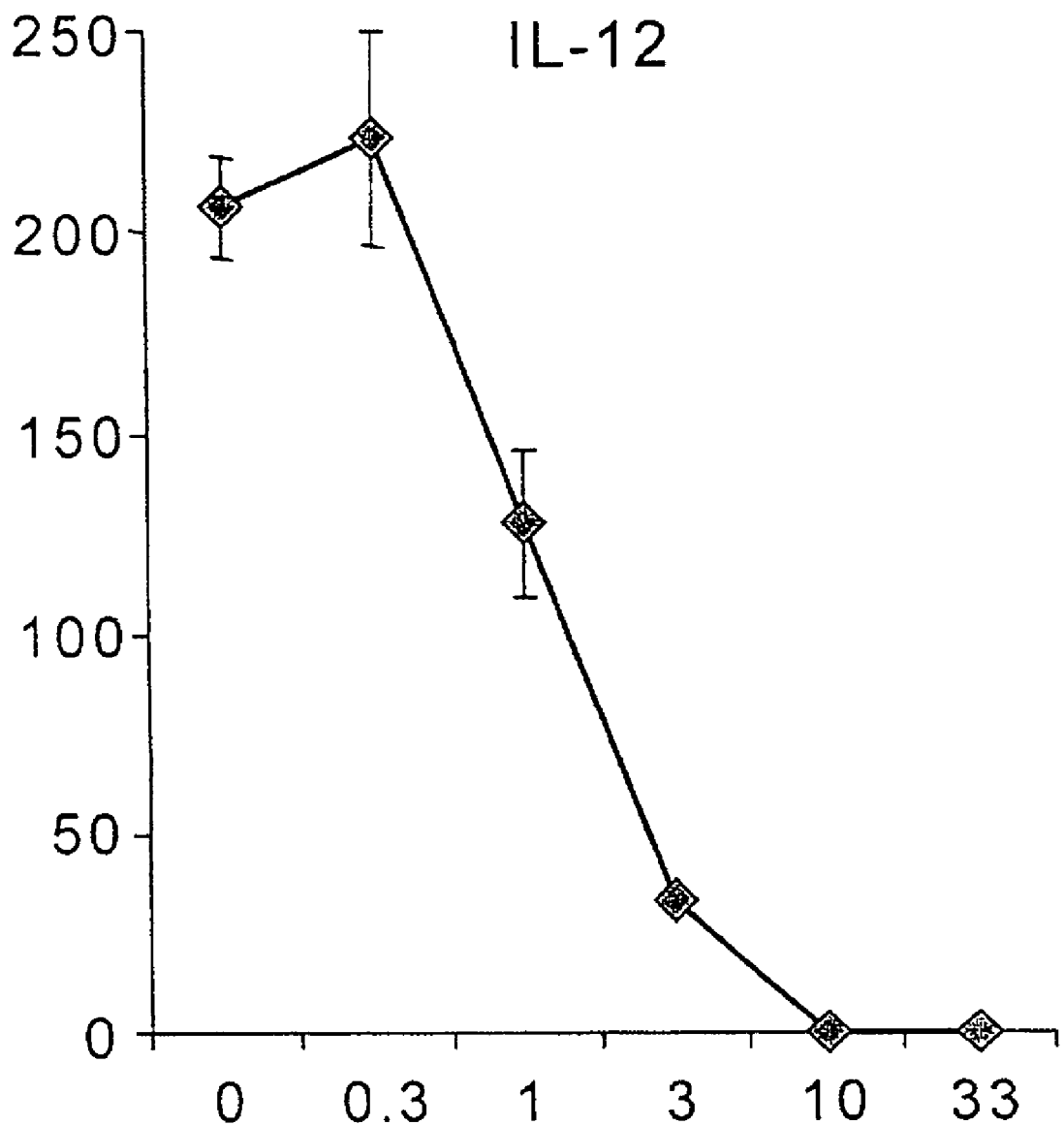
FIG. 13 shows the effect of LPS and IFN ated activation of B cells. These effects are absent when a mutant EtxB protein lacking GM1 binding activity is employed.
Figure 14:
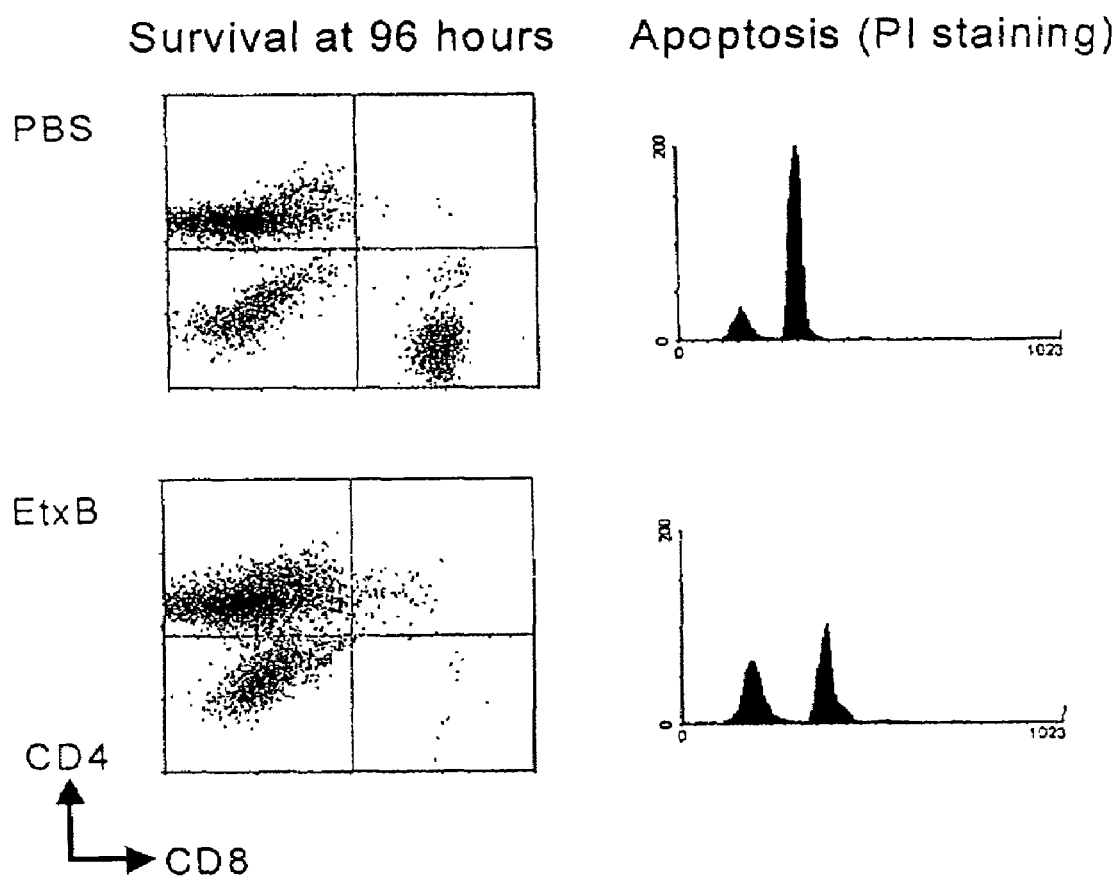
Figure 15:
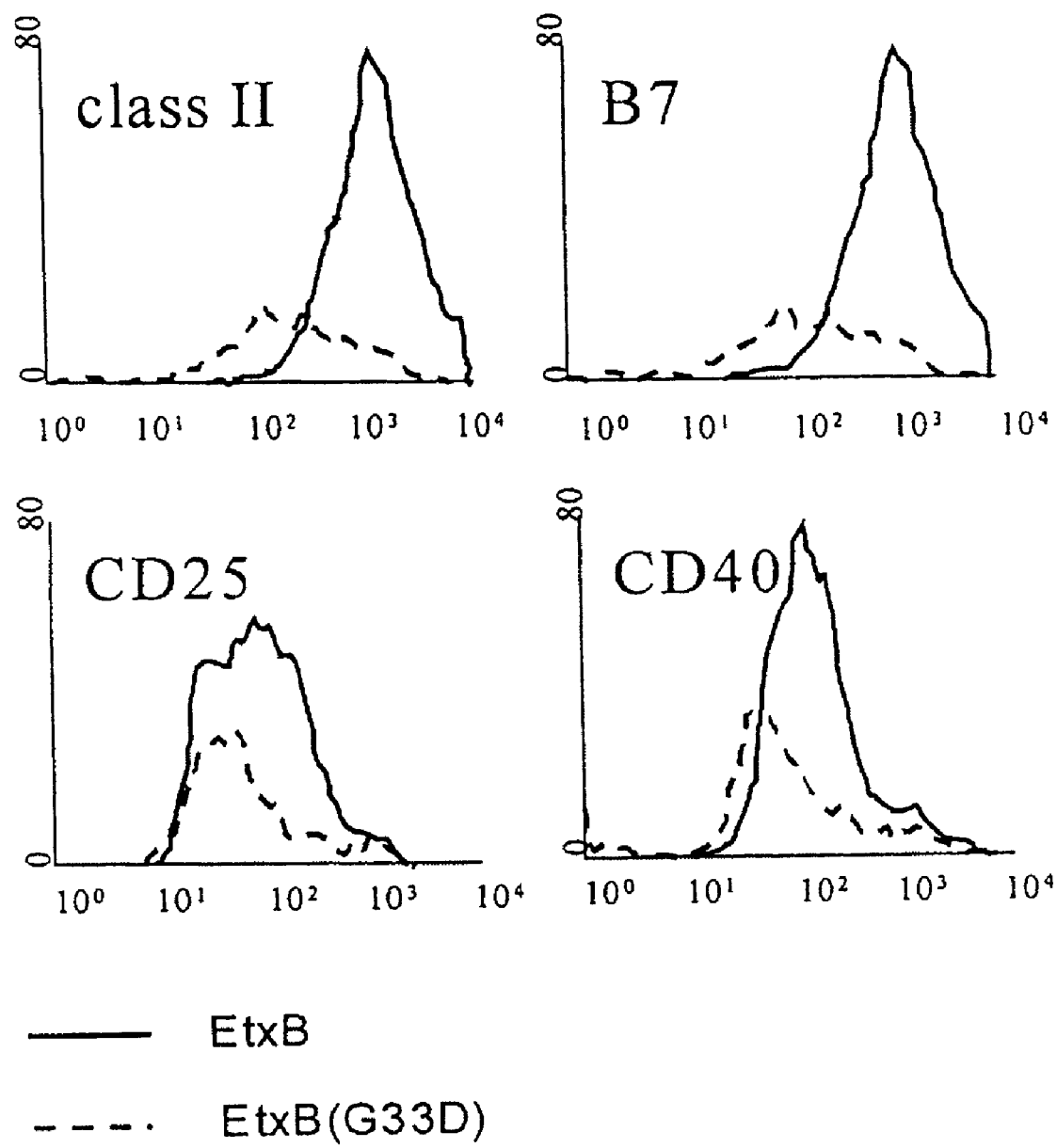
Figure 16:
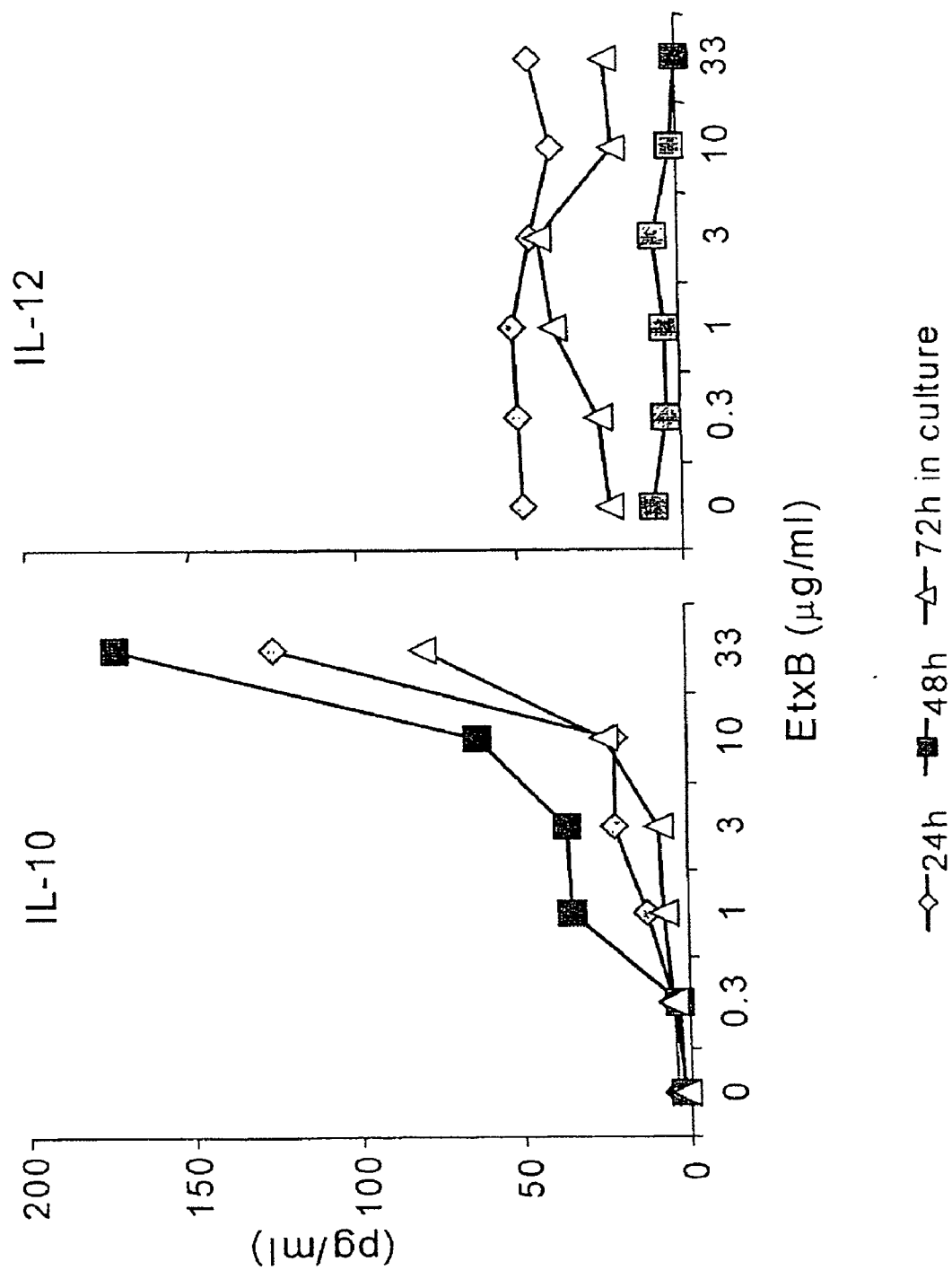
Figure 17:
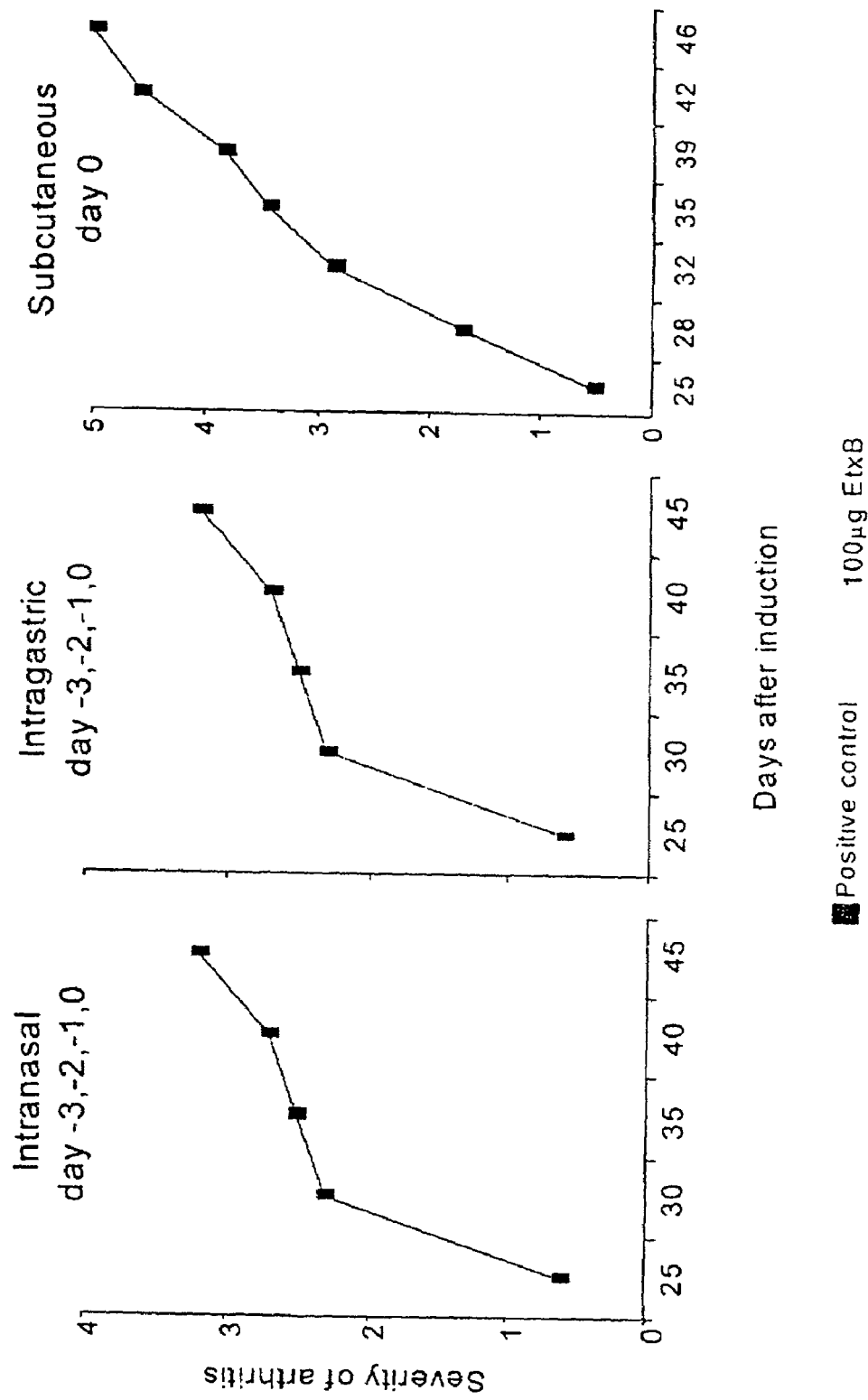
Figure 20:
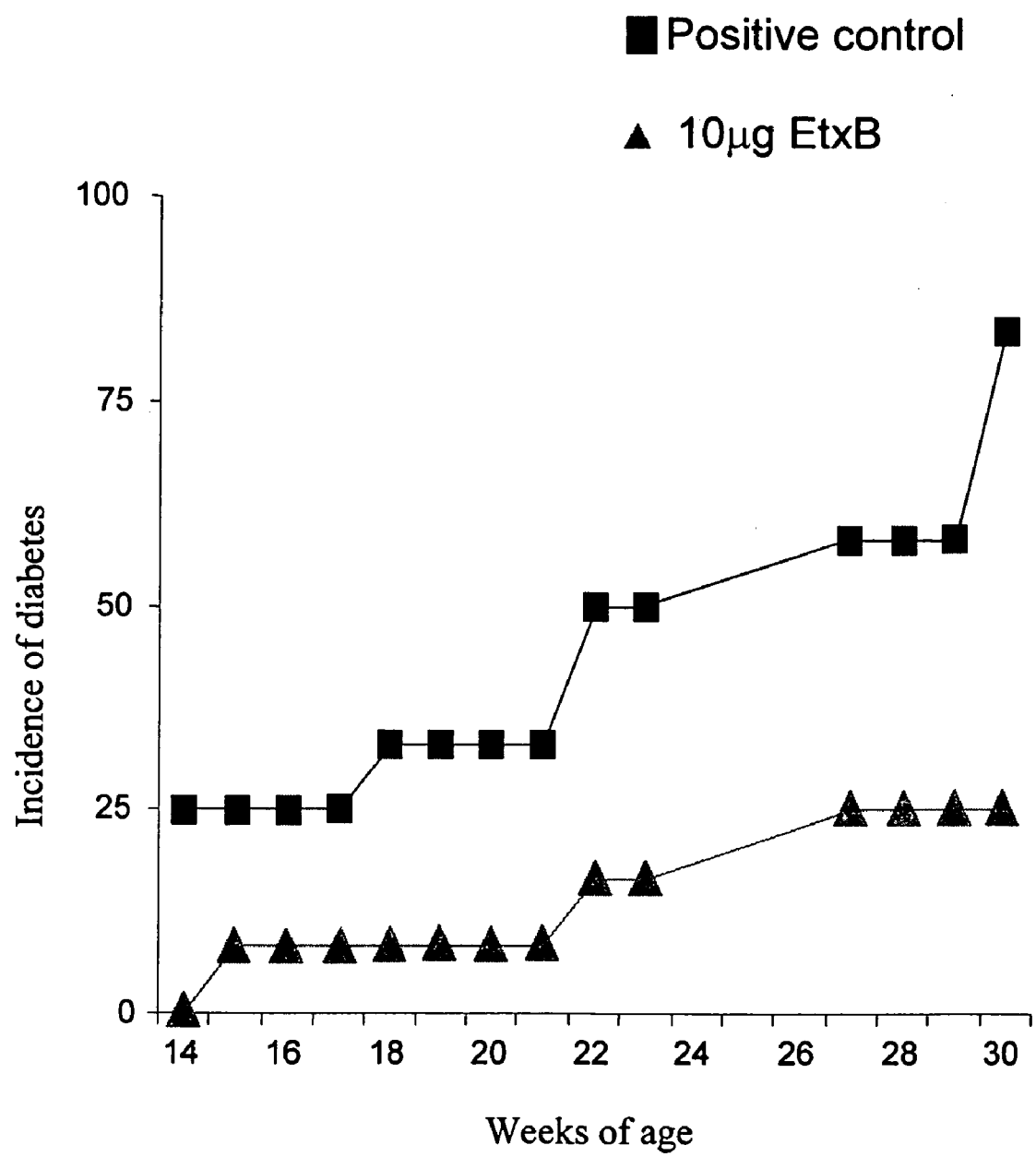

The results obtained are illustrated in FIGS. 9a and 9b. These show that EtxB, but not EtxB(G33D), dramatically protects mice from the development of collagen-induced arthritis.

Example 4A

Two separate human buffy coat samples (obtained from normal human blood donors) were used as a source of mononuclear cells. Cells were isolated over Ficoll-paque and washed extensively before culture in the absence of antigen or with 80 g/ml of either EtxB or EtxB(G33D) as indicated. Prior to culture the cell populations comprised 24% CD8+, 27% CD4+ and 27% CD8+, 22.9% CD4+ for each sample respectively. After culture for 18 hours the appearance of apoptotic cells was assessed in samples of cells stained with acridine orange (as detailed under Example 2). The results obtained are shown in FIG. 10; these illustrate that EtxB but not EtxB(G33D) induces apoptosis in a population of normal human peripheral blood mononuclear cells.

Example 4B

The murine T cell line, CTLL-2, was cultured to confluence and then the cells washed before being reseeded at $1 \times 10^6$ cells/ml in the absence of antigen or with 80 g/ml of either EtxB or EtxB(G33D) as indicated. After 18 hours samples were removed and the percentage of cells showing signs of apoptosis was assessed using acridine orange (detailed under Example 2). The results obtained are illustrated in FIG. 11. They show that cross-linking of GM1 leads to apoptosis in a proportion of murine CTLL cells.

TABLE 1

Lymphocyte proliferation in the presence of EtxB or EtxB (G33D)

| Dose μg/ml | EtxB | EtxB(G33D) | EtxB* | EtxB(G33D)* |
|---|---|---|---|---|
| 0 | 117.9 | 146.8 | 124.5 | 116.1 |
|   | (7.9) | (3.5) | (14.6) | (6.35) |
| 5 | 4928 | 2860 | 2424 | 1431.5 |
|   | (98.7) | (3.8) | (88.3) | (37.5) |
| 10 | 6978 | 3681 | 2518 | 4231 |
|   | (30.6) | (4.6) | (21.6) | (96.4) |
| 20 | 7084 | 6912 | 4394 | 5075 |
|   | (100) | (47.3) | (42.1) | (24.8) |
| 40 | 8844 | 8586 | 7431 | 4368.5 |
|   | (26) | (143.7) | (45.3) | (118.9) |
| 80 | 10246 | 12510 | 7986 | 7276 |
|   | (30.7) | (121.8) | (210.3) | (369.5) |
| 160 | 11311 | 13525 | — | — |
|   | (247) | (352.7) |   |   |

Mice were injected i.p. with 30 μg of EtxB (G33D) in complete Freund's adjuvant (CFA). Mesenteric lymph nodes were isolated 10 days later. Cells were isolated and incubated for 4 days in the presence of EtxB, EtxB (G33D) or disassembled monomeric forms of these proteins (*), generated by heating at 95° C. Proliferation was determined by addition of 1 μCi of ($^3$H) dThd for the last 6 hours on day 4. Data represents mean cpm and SEM of triplicate wells. Cells isolated from unimmunized mice gave <1500 cpm (dose 160 μg/ml).

TABLE 2

Cytokine analysis in the presence of EtxB or EtxB (G33D)

| Protein | IL-2 (pg/ml) | IFN- (pg/ml) |
|---|---|---|
| EtxB | 318 | 2700 |
| EtxB (G33D) | 67 | 4068 |

Mice were injected with EtxB (G33D) in CFA and mesenteric lymph nodes cells were isolated 10 days later. Cells were then incubated in vitro with either EtxB or EtxB(G33D) and samples of supernatants analysed for cytokine content on day 5 of cellular proliferation.

TABLE 3

EtxB-receptor mediated apoptosis in fractionated lymphocyes.

| Cells | Time (h) | No antigen | EtxB(G33D) | EtxB |
|---|---|---|---|---|
| MLNC | 4 | 0$^a$ (8) | 2 (0) | 1 (3) |
|   | 18 | 8 (10) | 5 (18) | 29 (35) |
| SPLTC | 4 | 3 (7) | 2 (6) | 3 (5) |
|   | 18 | 17 (5) | 16.5 (12) | 31 (32) |
| Negative selection |  |  |  |  |
| CD4 | 18 | 5 (37) | 6 (31) | 9 (35) |
| CD8 | 18 | 18 (11) | 19 (15) | 76 (73) |
| Positive selection |  |  |  |  |
| CD4 | 18 | 6 | 4 | 6 |
| CD8 | 18 | 7 | 7 | 60 |

$^a$Percentage apoptotic cells

Nuclear morphological changes in fractionated CD4 and CD8$^+$ T cells after 4 or 18 h incubation in the absence of antigen, or with 80 μg/ml of EtxB or EtxB(G33D) were examined by fluorescence microscopy following staining with acridine orange. Whole MLN were depleted of adherent cells. SPLTC were isolated by negative selection in glass beads column coated with mouse γ-globulins and rabbit anti-mouse as a secondary antibody. Fractionated SPLTC were obtained following labelling with rat phycoerythrin-anti-mouse CD4 or FITC-anti-mouse CD8α which were then incubated with MACS colloidal super-paramagnetic micro-beads conjugated with goat anti-rat IgG (H+L) F(ab )$_2$. These were separated using mini-MACS columns to obtain both the positively (>99% pure) and negatively (>90% pure) selected fractions of CD4 and CD8$^+$ T cells. Nuclear morphological changes were examined from 4 to 18 h in a random sample of 200 cells per treatment as described in the legend to FIG. 7. Maximum percentage of apoptotic cells occurred after 18 h. The data in brackets when indicated represent results from another separate experiment. Data for MLN and SPLTC are representative of a total of four experiments.

Percentage Apoptotic Cells

Eamples 8-12

Relating to Diabetes

Insulin dependent diabetes mellitus (IDDM) is an autoimmune disease resulting form the T-cell dependent destruction of insulin-producing cells from the pancreas Langerhans islets (1). It affects about 4 million people in Europe and North America alone and usually appears before the age of 30. There is no cure. Sufferers must give themselves daily insulin injections to control their blood glucose levels. It is unclear what triggers the immune system's attack on the islet cells because the regulation of the auto-aggressive immune response is complex, resulting from the interaction between several T cell subsets and their activation of mononuclear phagocytes. Islet destruction, both in humans and rodents, is attributed to the existence of auto-reactive CD4+T cells that recognise islet antigens and belong to the Th1 subset (i.e. secrete inflammatory cytokines such as IFNγ) (2). Such cells could be isolated from diabetic rodent spleens or pancreas inflammatory infiltrates and transferred the disease to syngenic receipents (3).

Research Design and Methods

Mice. NOD mice were purchased from Jackson Laboratories (Bar Harbor, USA) and were subsequently bred in our animal facilities under sterile conditions. Spontaneous diabetes in female mice from our colony appears around 12 weeks of age and reaches 80-90% by 30 weeks. Diabetes was characterised by weight loss and glucosuria levels above 111 mmol/l on three consecutive measurements one week apart. Glucosuria was measured using Diastix® strips from Bayer (Newbury, UK).

Proteins. EtxB was produced by expression in a marine Vibrio followed by purification from the culture supernatant. Insulin, purified from porcine pancreas (Sigma, Poole, UK) was dissolved in phosphate-buffered saline (pH 7.4) and admixed with EtxB immediately before administration.

Nasal administration protocol. Female NOD mice were given 6 doses of the treatments described on alternate days, over two weeks. Briefly, light anaesthesia was induced by inhalation using Halothane-RM* (Rhone-Merieux, Harlow, UK), the 20 1 dose was placed on the tip of the nose and was taken up with the respiratory movements.

Cytokine secretion assessment. IFNγ, IL-4 and IL-10 secretion by activated cells from the pancreatic lymph nodes was measured by cellular sandwich ELISAs. Briefly, a single cell suspension ($2 \times 10^6$/ml/well) from the pancreatic lymph nodes was cultured for 48 h on mouse anti-CD3-coated (clone 7D6, 10 µg/ml) 24-well plates. MaxiSorp™ ELISA plates from Nunc (Roskilde, Denmark) were coated overnight at 4° C. with capture antibody, then lymphocyte suspension was transferred to the ELISA plate and further incubated for 24 h. The plates were then washed and captured cytokines were detected using biotinylated anti-cytokine detection antibodies and the streptavidin-peroxidase detection system (3).

Diabetes adoptive transfer. 5 6-week old female NOD mice were given 6 doses of 10 ug insulin+10 ug EtxB in 20 ul PBS or PBS only (on alternate days, over two weeks). One day after the last treatment, spleens were collected, pooled and CD4+ T lymphocytes were isolated using CD4 (L3T4) MicroBeads from Miltenyi Biotec (Bisly, UK) according to the manufacturer's recommendations. $5 \times 10^6$ CD4+ purified T cells from either Insulin+EtxB or PBS only-treated mice were then mixed with an equal number of spleen cells from diabetic NOD female mice and injected intravenously to 8 week-old, 7,5 Gy-pre-irradiated female NOD mice. Glucosuria was then assessed every other day using Diastix® strips and mice were considered as diabetic after four consecutive measurements showed glucosuria levels above 111 mmol/l.

Insulitis assessment. Insulitis was assessed by histology. Pancreases were collected, fixed in neutral buffered formalin, embedded in paraffin, cut and stained with hematoxylin and eosin. Slides were viewed by light microscopy and 10-30 islets from at least two sections 100 um apart from each mouse were scored in a double blinded fashion. Based on the severity of insulitis, each islet was scored from 1 to 5 as follows: 1=free of insulitis; 2=peri-insulitis; 3=moderate insulitis (less than 50% of the islet is infiltrated); 4=severe insulitis (more than 50% of the islet is infiltrated) and 5=complete islet destruction with very few islet cells visible.

Example 5

Repeated nasal or oral administration of relatively high doses of insulin was shown to induce a regulatory CD4+ T cell population that prevents diabetes mellitus (4).

Results. Surprisingly, the present invention demonstrates that: (i) when a sub-optimal insulin administration protocol was used (6×10 ug doses on alternate days over 2 weeks) NOD mice were not protected; (ii) when similar doses of EtxB, were administered i.n. according to the same schedule, this did not prevent the development of IDDM in the NOD mice; (iii) however, admixed insulin+EtxB did lead to a decreased incidence of IDDM FIG. 23).

Summary. Intranasal administration of admixed insulin and EtxB to 6 week old NOD mice prevented the onset of diabetes mellitus.

Example 6

Islet-reactive T cells localise preferentially in the pancreatic lymph nodes (PLN), so autoreactive immune responses and their type are best investigated by assessing the cytokine secretion of PLN lymphocytes. We collected PLN from the NOD mice after the described treatment with insulin or EtxB or an admixture of these and investigated cytokine secretion from lymphocytes after activation with anti-CD3 as described (5).

Figure 24:
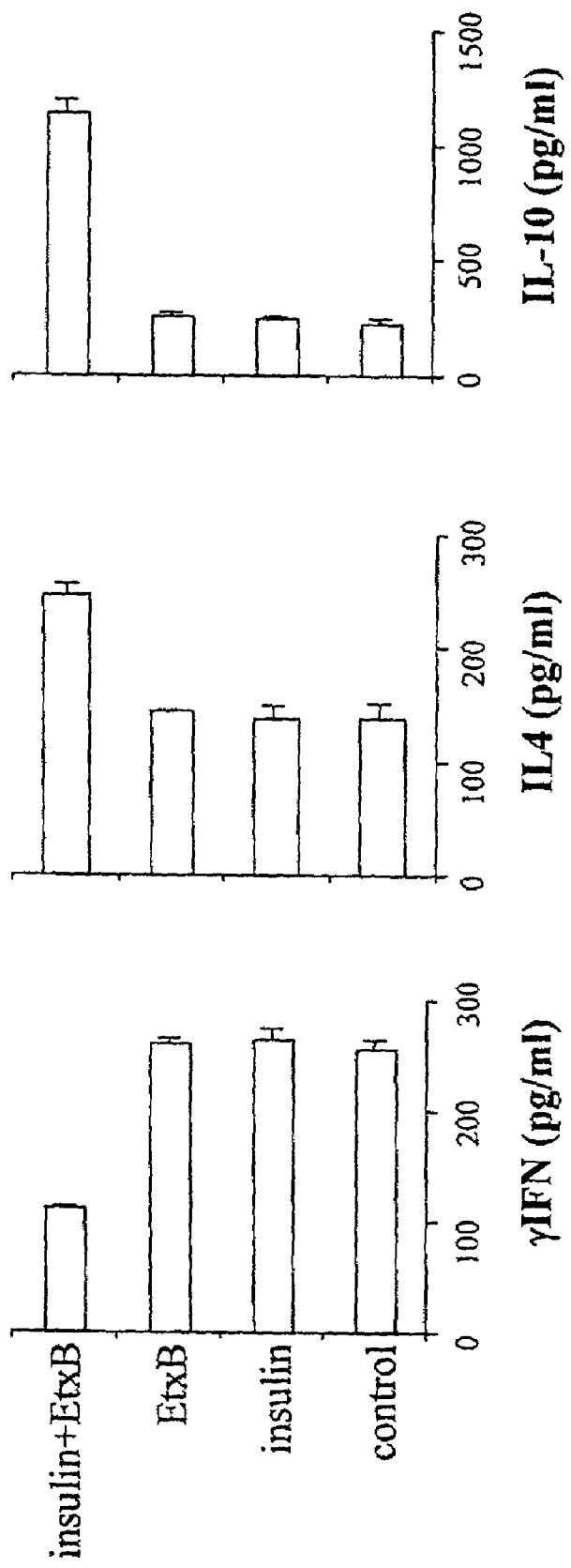

Results. We found a decrease of IFNγ secretion and an increase of IL-4 and IL-10 in the insulin+EtxB-treated mice when compared with those left untreated or treated with either insulin or EtxB alone (FIG. 24) while TGFβ secretion was not influenced by any treatment (data not shown).

Summary. Pancreatic lymph node cells from NOD mice protected against diabetes mellitus by insulin+EtxB treatment secrete less IFNγ and more IL-4 and IL-10 than the unprotected ones.

Example 7

In order to assess the effect of insulin+EtxB-treatment upon islet infiltration, we treated the mice as previously described, then collected the pancreas when mice (n=3 per time point) were 6, 12, 18 and 24 weeks of age.

Figure 25:
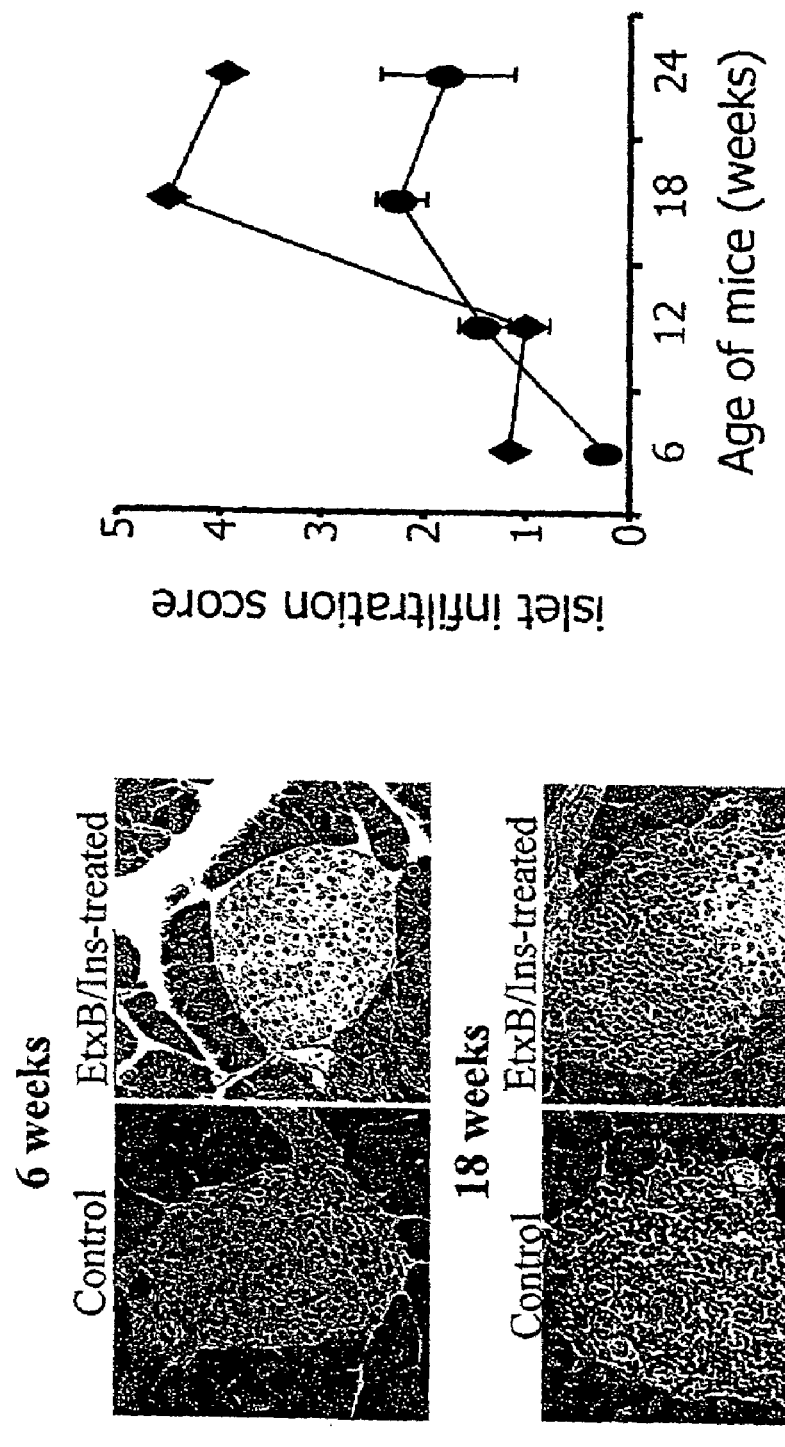
Figure 26:
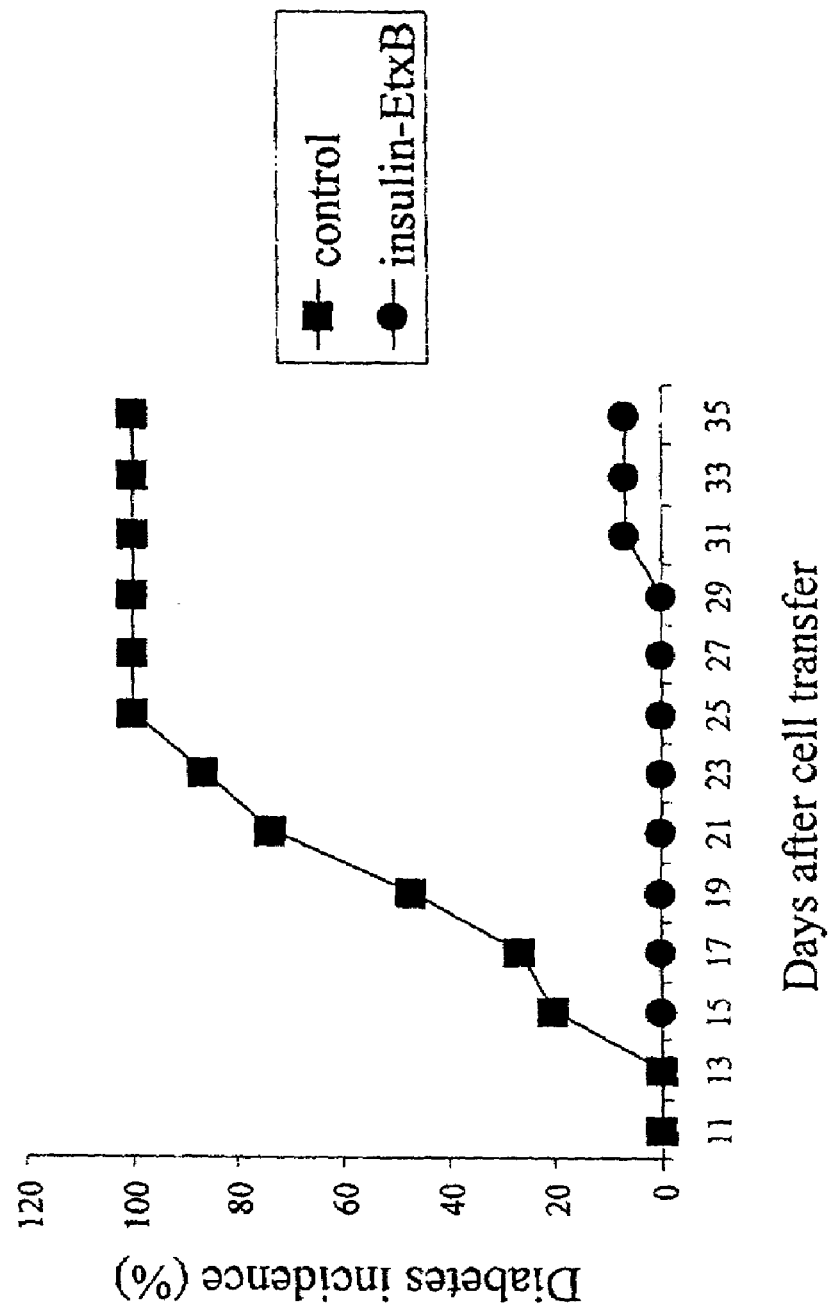
Figure 27:
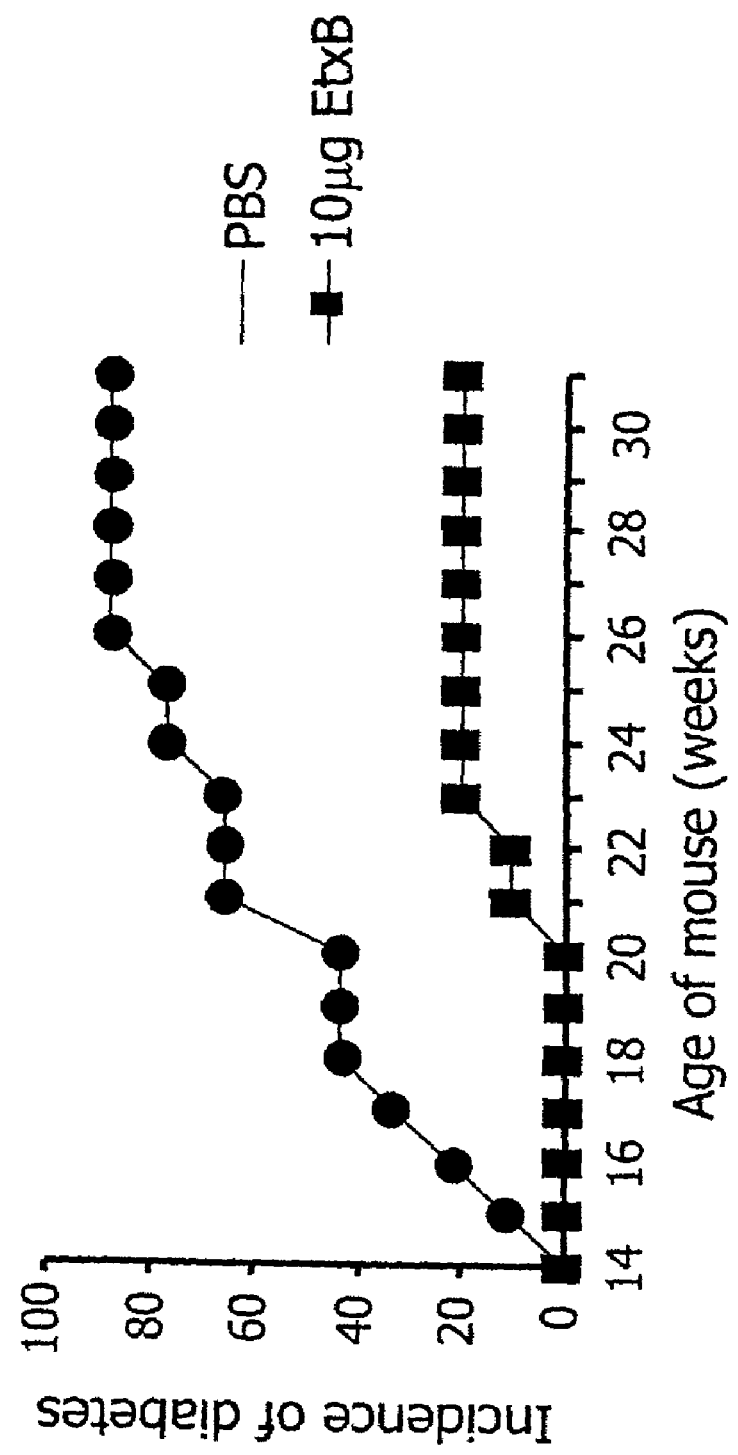
Figure 28:
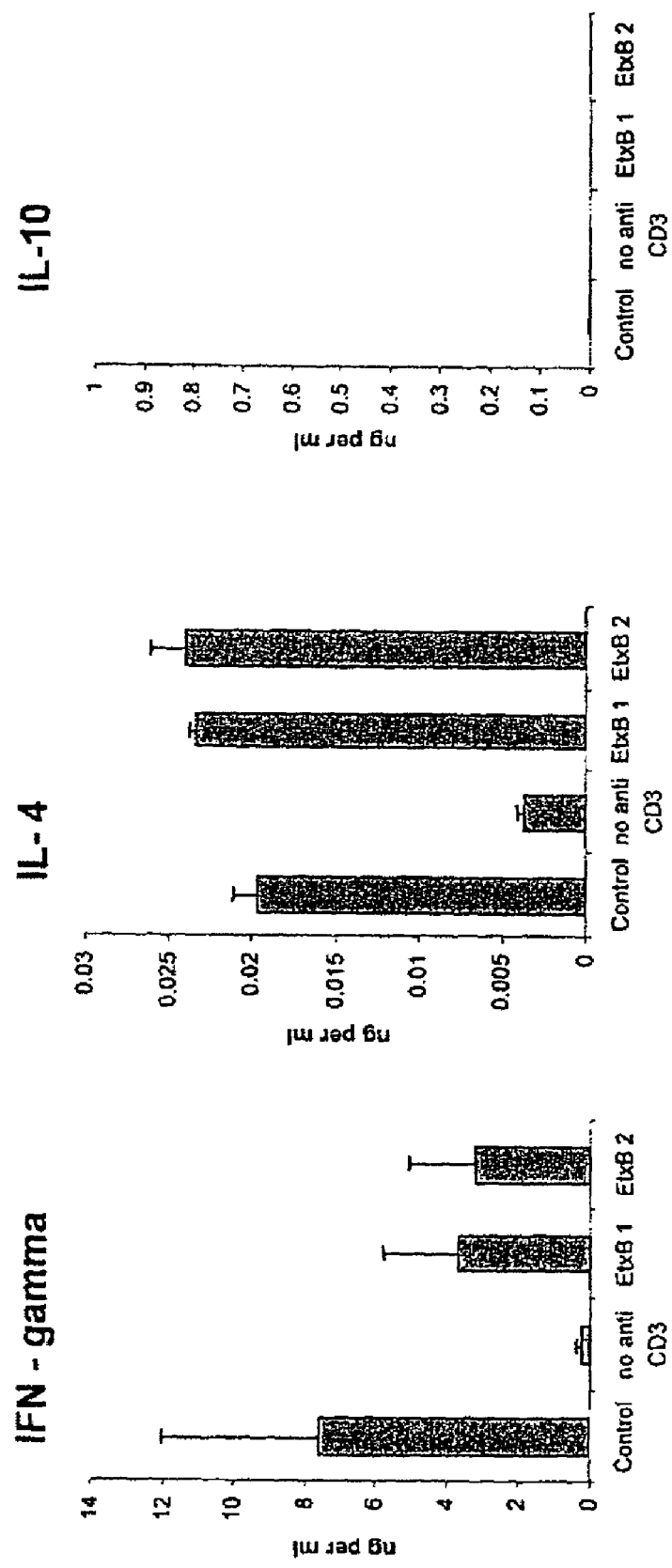

Results. Histological examination of hematoxylin-eosin-stained sections showed a lower degree of inflammatory infiltrate in the insulin+EtxB-treated mice when compared with those left untreated or treated with either insulin or EtxB alone (FIG. 25).

Summary. Protection against diabetes mellitus is associated with a lower degree of insulitis.

Example 8

In order to investigate whether the effect of insulin+EtxB leads to a long-lasting protection mediated by regulatory cells, we co-transferred splenocytes from recently diabetic mice with equal numbers of CD4+ cells from mice that were either treated with insulin+EtxB or left untreated to 7.5 Gy-irradiated mice.

Results. CD4+ T cells from the untreated mice could not prevent the rapid development of IDDM induced by the autoreactive cells from the recently diabetic ones. Conversely, insulin+EtxB leads to the development of a CD4+ regulatory cell population that prevents the development of IDDM. Long-term assessment data (FIG. 24) supports this finding, suggesting that protection is long-term and does not represent a mere delay of the disease.

Summary. Nasal treatment with insulin+EtxB generates regulatory CD4+ cells that transfer protection.

Example 9

Thirty days after cell transfer (when all the mice that received splenocytes from diabetic mice+CD4+ cells from untreated mice have developed IDDM), their pancreases were collected and their insulitis degree was assessed by histology. PLN were also collected and cytokine secretion from activated lymphocytes was assessed.

Results. The data obtained (Table 4-FIG. 29) shows that the transferred regulatory cells from the insulin+EtxB-treated mice lead to a decrease of IFNγ secretion and an increase of IL-4 and IL-10 and a decrease of insulitis grade.

Summary. Transferred protection is associated with a lower degree of insulitis and a Th2-skewed cytokine secretion profile.

Example 10

The finding that EtxB was not able to prevent diabetes in the NOD mouse when given in the absence of added insulin at 6 weeks of age, contrasted with our findings from models of arthritis. In CIA, as little as 1 μg of EtxB given on four occasions was sufficient to block the progression of disease. We hypothesised that the timing of administration may be key to the differences observed between the models. It is conceivable that EtxB triggers the activation of regulatory cell populations which are only active over a relatively short period of time. In order to test this, we delayed treatment of NOD mice until they had reached 10-12 weeks of age. By this time, peri-insulitis is well established and the immune response to islet antigens has been induced.

Results. Our findings showed that 6 treatments with 10 μg EtxB i.n. (a dose which was ineffective when given at 6 weeks of age) was now able to dramatically reduce the incidence of IDDM (FIG. 27). This suggests that EtxB can effectively block diabetes when given in the absence of autoantigen, but that pancreatic inflammation needs to be established in order for it to do so.

Summary. Once islet inflammation is already established, EtxB is able to prevent IDDM in the NOD mouse when given alone.

Example 11

The prevention of IDDM following administration of EtxB admixed with insulin at 6 weeks, was associated with a clear Th1 to Th2 switch in the cytokine profile of pancreatic T cells responding to TCR engagement. In order to determine whether prevention of IDDM following the late administration of EtxB alone was associated with a similar shift, we carried out an identical assessment of pancreatic lymph node cell function.

Results. The results revealed a marked difference from those reported above. Whereas the late administration of EtxB led to a dramatic reduction in the production of Th1-associated γIFN as was seen with earlier treatment with EtxB+insulin, this was not associated with a concomitant rise in Th2 cytokine secretion. Instead, the levels of IL-4 were unchanged and IL-10 was not detected either in lymph node cell cultures from treated or untreated animals (FIG. 28). This findings suggests that the mechanisms of IDDM prevention by EtxB alone and EtxB+insulin may be different. In the latter case EtxB is acting as an 'adjuvant' promoting immune deviation away from Th1 and toward Th2. In the former case, the Th1 response is being suppressed without promotion of a Th2 response.

Summary. Altered pancreatic lymph node cytokine production in response to late administration of EtxB alone.

Example 12

The effectiveness of the B-subunit in treating autoimmune diabetes has been established using the NOD mouse model in which disease arises spontaneously at between 14 and 25 weeks of age. As in human type I diabetes, disease in the NOD is influenced by complex genetic and environmental factors which allow the development if an immune response to several pancreatic antigens. The mice develop a non-specific insulitis (immune infiltration of the pancreas) at between 6 and 8 weeks of age, and this leads to progressive islet destruction such that 70 to 80% become diabetic. Diabetes is readily demonstrated by the presence of high glucose levels in the urine or blood.

Results The present inventors have demonstrated that injection of the B-subunit into NOD mice during the time at which insulitis is becoming established can block the progression to diabetes, preserving insulin levels and reducing islet destruction (FIG. 20).

Summary

The present invention demonstrates that as a result of its ability to bind to receptors on mammalian cells, EtxB is able to modulate the function of a variety of cells involved in the induction and maintenance of immune responses. This activity allows it to subtly alter local micro-environmental conditions which can dramatically change the nature of immunity, and forms the basis of its usefulness in treating autoimmune diseases, such as diabetes and infectious diseases. The use of the B subunit is advantageous because it is a protein which is readily produced in batch fermentation cultures of bacteria, is exceptionally thermo-stable and acid stable and can withstand lyophilisation and long term storage. In addition, the use of pure recombinantly produced B-subunit, which is devoid of A-subunit is also advantageous because it has been shown to be completely unable to cause any toxic effect in humans.

Given the effectiveness of the B-subunit in treating both arthritis and diabetes, EtxB may prove to be similarly effective in blocking other Th1 mediated autoimmune diseases such as multiple sclerosis and inflammatory bowel disease. The disease protection experiments described have been carried out in animal models to date. These models are well characterised and closely mimic the human counterpart diseases. In addition, a large body of data indicates that human immune cells are modulated by EtxB in vitro in ways identical to those noted in the animal experiments. Taken together these data provide a firm basis for the use of EtxB in treating human disease.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or biology or related fields are intended to be covered by the present invention. All publications mentioned in the this specification are hereby incorporated herein in their entireties by reference.

REFERENCES

1. Wong F S, Janeway C A Jr.: Insulin-dependent diabetes mellitus and its animal models. *Curr. Opin. Immunol.* 11:643-647, 1999.
2. Wang B, Andre I, Gonzalez A, Katz J D, Aguet M, Benoist C, Mathis D: Interferon-gamma impacts at multiple points during the progression of autoimmune diabetes. *Proc. Natl. Acad. Sci. USA* 94:13844-13849, 1997.
3. Beech J T, Bainbridge T, Thompson S J: Incorporation of cells into an ELISA system enhances antigen driven lymphokine detection *J. Immunol. Meth.* 205:163-168, 1997.

4. Zhang Z J, Davidson L, Eisenbarth G, Weiner H L: Suppression of diabetes in nonobese diabetic mice by oral administration of porcine insulin. *Proc. Natl. Acad. Sci. USA* 88:10252-10256, 1991.Wicker L S, Miller B J, Mullen Y: Transfer of autoimmune diabetes mellitus with splenocytes from nonobese diabetic (NOD) mice. *Diabetes* 35:855-860, 1986.

5. Ploix C, Bergerot I, Durand A, Czerkinsky C, Holmgren J, Thivolet C: Oral administration of cholera toxin B-insulin conjugates protects NOD mice from autoimmune diabetes by inducing CD4+ regulatory T-cells. *Diabetes* 48:2150-2156, 1999.

The above description is for the purpose of teaching the person of ordinary skill in the art how to practice the present invention, and is not intended to detail all thos obvious modifications and variations of which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The invention claimed is:

1. A method for reducing incidence or progression of insulin dependent diabetes mellitus (IDDM) by modulating an immune response in a mammalian subject in need of prevention against or treatment of diabetes wherein the method comprises administering to the mammalian subject an effective amount of EtxB and insulin.

2. A method according to claim 1 wherein the modulation of the immune response is determined by measuring a change in at least one parameter selected from the group consisting of: a change in Th2 associated cytokine levels, a change in antigen specific T-cell reactivity, a change in Th1 associated cytokine levels and any combination thereof.

3. A method according to claim 1 wherein the modulation of the immune response is determined by measuring a change in the production of Th1 associated cytokines.

4. A method according to claim 3 wherein the Th1 associated cytokine is IFNγ.

5. A method according to claim 1 wherein the modulation of the immune response is determined by measuring a change in the production of Th2 associated cytokines.

6. A method according to claim 5 wherein the Th2 associated cytokine is selected from the group consisting of IL-4 and IL-10 cytokines and any combination thereof 7. A method according to claim 1 wherein the modulation of the immune response is determined by measuring a change in cytokines associated with T regulatory cell.

8. A method according to claim 7 wherein the cytokines are selected from the group consisting of IL- 10 and TGFβ and any combination thereof.

9. A method in accordance with claim 1 wherein said step of administering to the mammalian subject comprises oral administration.

10. A method in accordance with claim 1 wherein said step of administering to the mammalian subject comprises parenteral administration.

11. A method in accordance with claim 1 wherein said step of administering to the mammalian subject comprises intranasal administration.

12. A method for reducing incidence or progression of insulin dependent diabetes mellitus (IDDM) by modulating an immune response in a mammalian subject in need of prevention against or treatment of diabetes wherein the method comprises
  i) establishing that the mammalian subject is experiencing pancreatic islet inflammation and
  ii) administering to the mammalian subject having pancreatic islet inflammation an effective amount of EtxB.

13. A method in accordance with claim 12 wherein said step of administering to the mammalian subject comprises oral administration.

14. A method in accordance with claim 12 wherein said step of administering to the mammalian subject comprises parenteral administration.

15. A method in accordance with claim 12 wherein said step of administering to the mammalian subject comprises intranasal administration.

16. A method according to claim 12 wherein the modulation of the immune response is determined by measuring a change in at least one parameter selected from the group consisting of: a change in Th2 associated cytokine levels, a change in antigen specific T-cell reactivity, a change in Th1 associated cytokine levels and any combination thereof.

17. A method according to claim 12 wherein the modulation of the immune response is determined by measuring a change in the production of Th1 associated cytokines.

18. A method according to claim 17 wherein the Th1 associated cytokine is JFNγ.

19. A method according to claim 12 wherein the modulation of the immune response is determined by measuring a change in the production of Th2 associated cytokines.

20. A method according to claim 19 wherein the Th2 associated cytokine is selected from the group consisting of IL-4 and IL-10 cytokines and any combination thereof.

21. A method according to claim 12 wherein the modulation of the immune response is determined by measuring a change in cytokines associated with T regulatory cell.

22. A method according to claim 21 wherein the cytokines are selected from the group consisting of IL-b and TGFβ and any combination thereof.

23. A method according to claim 1, wherein the mammalian subject is pre-diabetic.

24. A method according to claim 1, wherein the mammalian subject is diabetic.

25. A method according to claim 12, wherein the mammalian subject is pre-diabetic.

26. A method according to claim 12, wherein the mammalian subject is diabetic.

* * * * *